US012678033B2

(12) United States Patent
Nakamura et al.

(10) Patent No.: US 12,678,033 B2
(45) Date of Patent: Jul. 14, 2026

(54) ENDOSCOPE BENDING OPERATION MECHANISM AND ENDOSCOPE

(71) Applicant: OLYMPUS MEDICAL SYSTEMS CORP., Tokyo (JP)

(72) Inventors: Yuna Nakamura, Hachioji (JP); Kei Sekiya, Sagamihara (JP); Kyoko Iwaku, Hino (JP); Giichi Kaneta, Musashino (JP); Hisanobu Suzuki, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 286 days.

(21) Appl. No.: 18/389,253

(22) Filed: Nov. 14, 2023

(65) Prior Publication Data

US 2024/0156334 A1 May 16, 2024

Related U.S. Application Data

(60) Provisional application No. 63/425,357, filed on Nov. 15, 2022.

(51) Int. Cl.
*A61B 1/005* (2006.01)
(52) U.S. Cl.
CPC .................................. *A61B 1/0057* (2013.01)
(58) Field of Classification Search
CPC .................................................... A61B 1/0057
See application file for complete search history.

(56) References Cited

U.S. PATENT DOCUMENTS

| | | | | | |
|---|---|---|---|---|---|
| 4,825,850 | A | * | 5/1989 | Opie | A61B 1/0052 600/122 |
| 5,402,793 | A | * | 4/1995 | Gruner | A61B 1/0052 600/463 |
| 6,440,062 | B1 | * | 8/2002 | Ouchi | A61B 1/00098 600/146 |

(Continued)

FOREIGN PATENT DOCUMENTS

| | | |
|---|---|---|
| JP | 2000-126119 A | 5/2000 |
| JP | 5501703 B2 | 5/2014 |
| JP | 6329041 B2 | 5/2018 |

*Primary Examiner* — Michael J Carey
*Assistant Examiner* — Megan Elizabeth Monahan
(74) *Attorney, Agent, or Firm* — Morgan, Lewis & Bockius LLP

(57) ABSTRACT

An endoscope bending operation mechanism comprises an up-down bending operation knob (a left-right bending operation knob), an up-down bending pulley (a left-right bending pulley) supported for rotation by a pulley case, the up-down bending pulley is configured to move by an operation force from the up-down bending operation knob, an up-down bending operation wire (a left-right bending operation wire) having a proximal end and a distal end, the proximal end of which is connected to the up-down bending pulley (the left-right bending pulley) and the distal end of which is connected to a bending portion of an insertion section of an endoscope, a stopper member, a protruding portion, the stopper member and the protruding portion are movable relative to each other, an amount of relative rotation between the up-down bending pulley (the left-right bending pulley) and the pulley case is restricted by the protruding portion contacting the stopper member.

14 Claims, 35 Drawing Sheets

(56)                    References Cited

U.S. PATENT DOCUMENTS

|  |  |  |  |
|---|---|---|---|
| 6,491,627 B1 * | 12/2002 | Komi ................... | A61B 1/0052 |
|  |  |  | 600/149 |
| 8,137,308 B2 | 3/2012 | Schultz |  |
| 2013/0190566 A1 * | 7/2013 | Miyoshi ............. | A61B 1/00126 |
|  |  |  | 600/131 |
| 2016/0073856 A1 | 3/2016 | Saito |  |
| 2017/0238787 A1 * | 8/2017 | Hijihara ............... | A61B 1/0052 |
| 2023/0309796 A1 * | 10/2023 | Fancher ............... | A61B 1/0052 |
|  |  |  | 600/131 |

* cited by examiner

ENDOSCOPE BENDING OPERATION MECHANISM AND ENDOSCOPE

RELATED APPLICATION DATA

This application is based on and claims priority under 35 U.S.C. § 119 to U.S. Provisional Application No. 63/425,357 filed on Nov. 15, 2022, the entire contents of which are incorporated herein by reference.

FIELD OF THE DISCLOSURE

The present disclosure relates to an endoscope bending operation mechanism configured to bend a bending portion by a long member such as a bending operation wire, and an endoscope.

DESCRIPTION OF RELATED ART

These days, endoscopes are widely used in a medical field. An endoscope includes an elongated insertion section. An inside of a body cavity as a subject can be observed using the endoscope, by inserting the insertion section into the body cavity.

With an endoscope including a bending portion at an insertion section, a bending operation on the bending portion is performed using a bending operation mechanism provided at an operation section. For example, as disclosed in Japanese Patent No. 6329041, a bending operation mechanism includes a pulley that is turnably provided inside an operation section, and a bending operation wire that connects the pulley to a bending portion. Such a bending operation mechanism causes a winding amount of the bending operation wire on the pulley to be changed according to a turned state of the pulley. The bending operation mechanism can bend the bending portion based on a change in the winding amount.

SUMMARY OF THE DISCLOSURE

An endoscope bending operation mechanism according to an aspect of the present disclosure comprising: a bending operation controller; a pulley unit including a pulley supported for rotation by a pulley case, the pulley configured to move by an operation force from the bending operation controller; a wire, having a proximal end and a distal end, wherein the proximal end of the wire is connected to the pulley and the distal end of the wire is connected to a bending portion of an insertion section of an endoscope; and a movement limiter unit including a limit structure and a stopper structure, wherein the stopper structure and the limit structure are movable relative to each other, wherein an amount of relative rotation between the pulley and the pulley case is restricted by the stopper structure contacting the limit structure, wherein either (i) the limit structure is attachable to and detachable from the pulley case and the pulley includes the stopper structure or (ii) the limit structure is attachable to and detachable from the pulley and the pulley case includes the stopper structure.

An endoscope bending operation mechanism according to another aspect of the present disclosure comprising: a bending operation controller; a pulley unit including a pulley housing, a pulley, and a first pulley holder supporting the pulley for rotation, the first pulley holder fixed to the pulley housing and pulley operably attached to the bending operation controller, the pulley configured to move by an operation force from the bending operation controller; and a wire having a proximal end and a distal end, wherein the proximal end or the wire is connected to the pulley and the distal end of the wire is connected to the bending portion of an insertion section of an endoscope; wherein the pulley includes a first stopper structure and the first pulley holder includes a first limit structure, and wherein the first limit structure and the first stopper structure are configured to come into contact to restrict a rotation angle of the pulley to a first rotation angle.

An endoscope bending operation mechanism according to an aspect of the present disclosure comprising: a bending operation controller; a pulley configured to move by an operation force from the bending operation controller; a pulley case supporting the pulley for rotation; a wire having a proximal end and a distal end, wherein the proximal end of the wire is connected to the pulley and the distal end of the wire is connected to a bending portion of an insertion section of an endoscope; and one or more limit structure, wherein the pulley case includes a plurality of grooves, the one or more limit structure is inserted into the plurality of grooves.

BRIEF DESCRIPTION OF THE DRAWINGS

FIG. 10 is an exploded perspective view according to the first embodiment, and shows the bending operation mechanism main body from the other end side.

Figure 16:
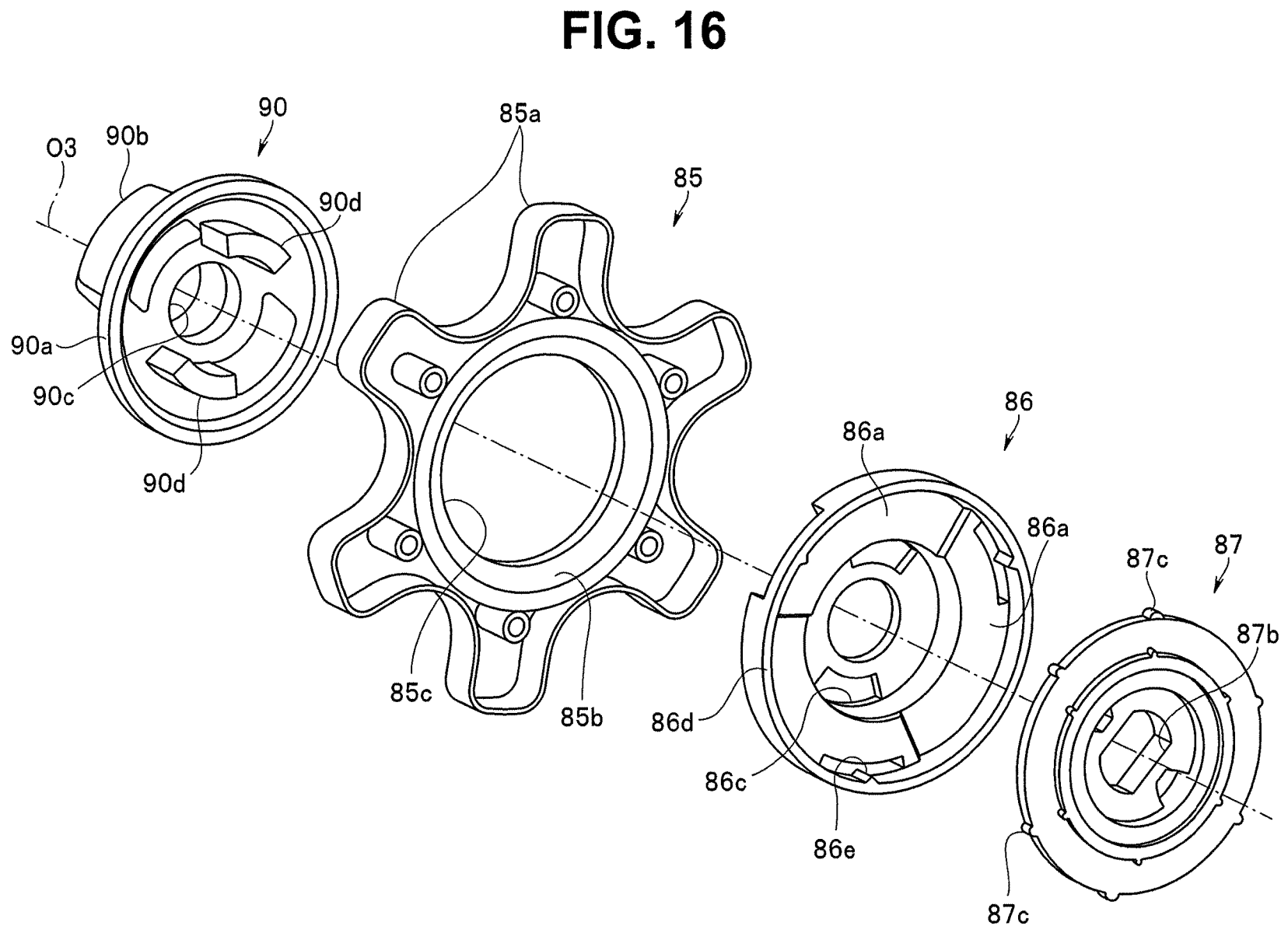

FIG. 16 is an exploded perspective view according to the first embodiment, and shows main parts of the left-right bending operation knob in an enlarged manner from the one end side.

DETAILED DESCRIPTION

Generally, an outer diameter, a length, and the like of an insertion section of an endoscope vary depending on an application part on a subject, intended usage, and the like. Furthermore, a bending angle required for a bending portion of the insertion section varies depending on the application part on the subject, the intended usage, and the like. Accordingly, dedicated parts designed for each model of endoscope are generally used as various structural parts that form a bending operation mechanism.

However, especially in relation to a single-use endoscope for medical use that is used just once, structural parts of the bending operation mechanism are desirably made common among models as much as possible to reduce manufacturing costs wherever possible. Moreover, to efficiently further reduce the manufacturing costs, an adjustment mechanism and the like for the bending angle and the like of the bending portion are desirably simplified.

According to the embodiments described below, an endoscope bending operation mechanism and an endoscope that have simple structures and that can be manufactured at a low cost by reducing the number of dedicated parts can be provided.

In the following, an embodiment of the present disclosure will be described with reference to the drawings. The drawings are according to an embodiment of the present disclosure, and FIG. 1 is a perspective view showing an endoscope.

Figure 1:
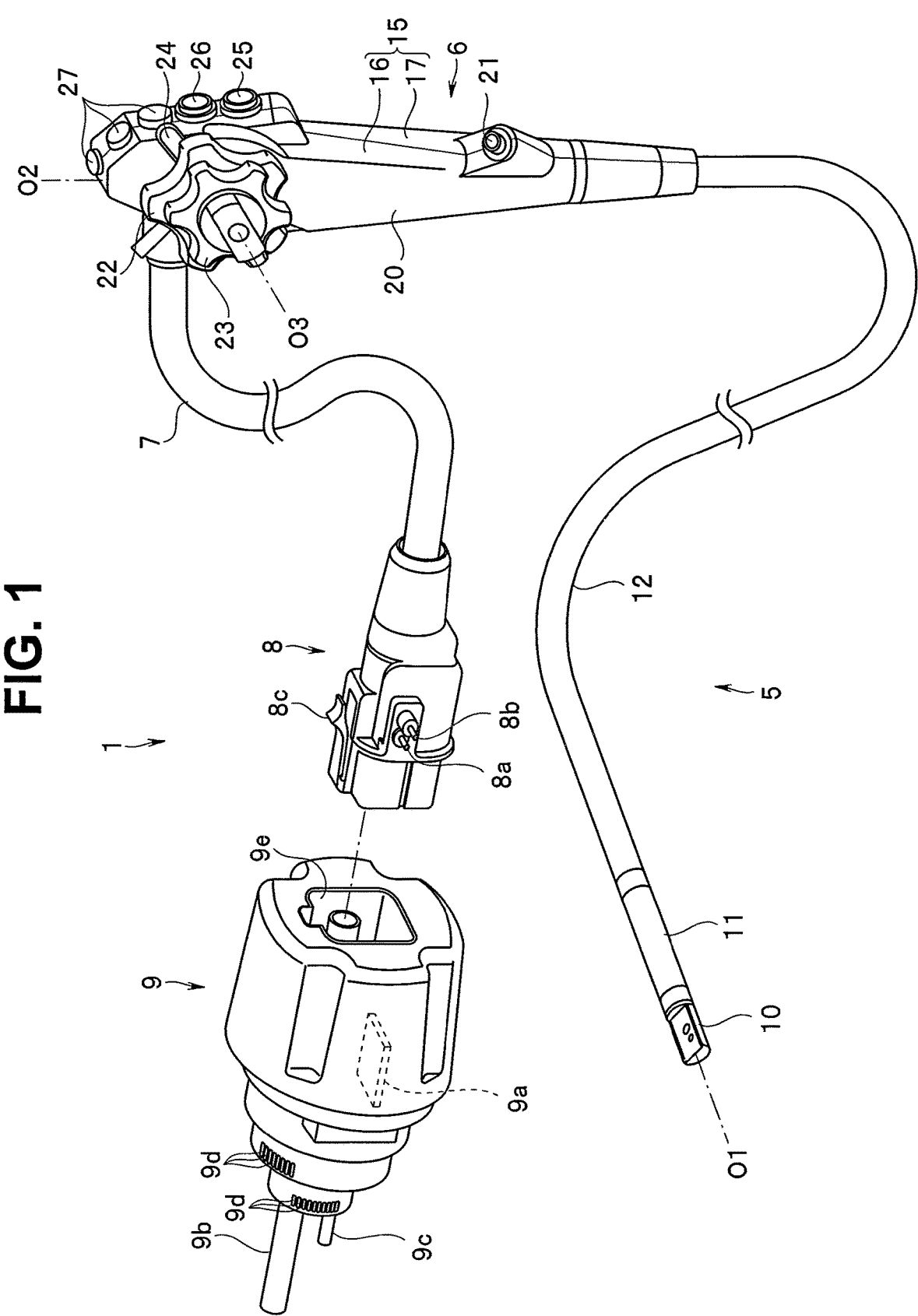
FIG. 1 is a perspective view according to a first embodiment, and shows an endoscope.

An endoscope 1 shown in FIG. 1 is a single-use endoscope for medical use that is used just once, for example. The endoscope 1 includes an insertion section 5, an operation section 6, a universal cord 7, and an endoscope connector 8.

The insertion section 5 includes, in order from a distal end side, a distal end portion 10, a bending portion 11, and a flexible tube portion 12.

Figure 2:
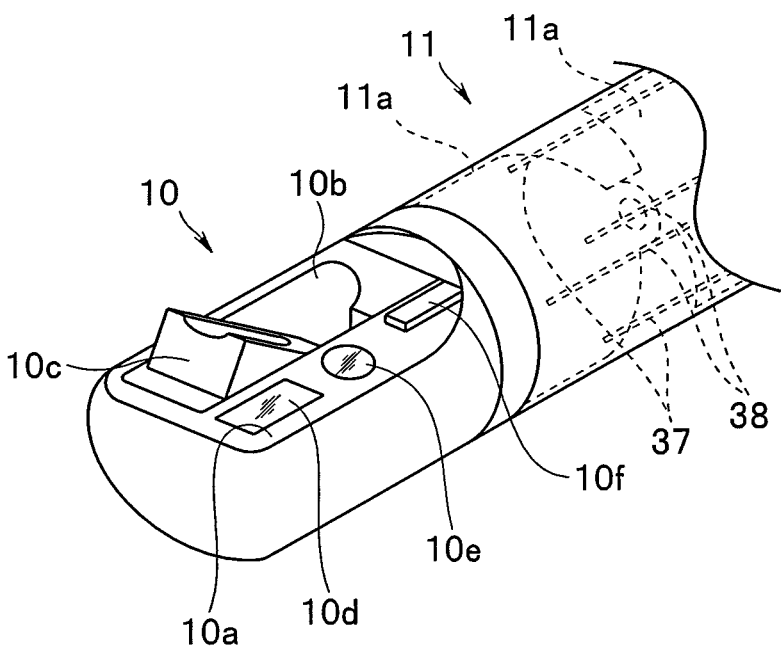
FIG. 2 is a perspective view according to the first embodiment, and shows a distal end portion.

As shown in FIG. 2, the distal end portion 10 is formed by a rigid member into a substantially cylindrical shape. The distal end portion 10 includes a flat portion 10a, an opening portion 10b, and a raising base 10c.

The flat portion 10a is formed at a part of the distal end portion 10, at an outer peripheral side portion. The flat portion 10a is provided with an illumination window 10d, an observation window 10e, and a nozzle 10f.

The illumination window 10d is formed by an optical member that is positioned at a distal most end of an illumination optical system. The illumination optical system is capable of radiating, on a subject, illumination light that is guided from a light source by a light guide or the like, for example.

The observation window 10e is formed by an observation optical system of an image pickup unit that is provided at the distal end portion 10. In other words, the observation window 10e is formed by causing an optical member positioned at a distalmost end of the observation optical system to be exposed from the flat portion 10a. The observation optical system takes in return light from the subject, from the observation window 10e. Then, the observation optical system projects the return light that is taken in, onto an image pickup device of the image pickup unit. Accordingly, the image pickup device is capable of picking up a subject image by converting the return light into an image pickup signal. Here, an optical axis of the observation optical system is set to a direction that intersects a longitudinal axis O1 of the insertion section 5 (that is, a lateral viewing direction).

The nozzle 10f is connected to an end portion on a distal end side of a gas/liquid feeding tube 47 (see FIG. 3) described later. The nozzle 10f is thereby allowed to discharge gas or liquid supplied from the gas/liquid feeding tube 47 to the flat portion 10a.

The opening portion 10b is formed to open in a side portion of the distal end portion 10 in an outer peripheral direction. The opening portion 10b communicates with a treatment instrument channel 31 described later.

The raising base 10c is a member for raising a distal end side of a treatment instrument protruding from the treatment instrument channel 31. Accordingly, the raising base 10c is disposed inside the opening portion 10b, at a position that faces a distal end of the treatment instrument channel 31. Furthermore, the raising base 10c is swingably attached to the distal end portion 10. Moreover, a distal end side of a raising base operation wire 42 described later is connected to the raising base 10c.

The bending portion 11 includes a plurality of bending pieces 11a (see FIG. 2). The bending pieces 11a are arranged in a row along the longitudinal axis O1 of the insertion section 5. Furthermore, of the bending pieces 11a, bending pieces 11a that are adjacent to each other are turnably coupled by a rivet or the like. The bending portion 11 is thus able to bend in every direction including up-down and left-right directions.

Furthermore, distal end portions of a pair of up-down bending operation wires 37 and distal end portions of a pair of left-right bending operation wires 38, each of the operation wires 37 and 38 being a long member, are each connected to the bending piece 11a that is positioned at a distalmost end of the bending portion 11.

Note that, in the present embodiment, up-down and left-right directions of the insertion section 5 are directions that intersect the longitudinal axis O1, for example, and are defined in association in a predetermined way with up-down and left-right directions of an image that is picked up by the image pickup device of the distal end portion 10.

The flexible tube portion 12 is a tube portion that is capable of warping according to a shape of a subject into which the insertion section 5 is inserted. In the present embodiment, a flexible endoscope including the flexible tube portion 12 is described as an example of the endoscope 1, but the endoscope 1 may instead be a rigid endoscope including a rigid tube portion.

The operation section 6 includes a housing 15 as an operation section main body. For example, the housing 15 is formed while being divided into left and right by including a first housing member 16 and a second housing member 17. The first and second housing members 16, 17 are formed by resin molding, for example. The first housing member 16 and the second housing member 17 are bonded by an adhesive or the like to form the hollow housing 15.

Figure 4:
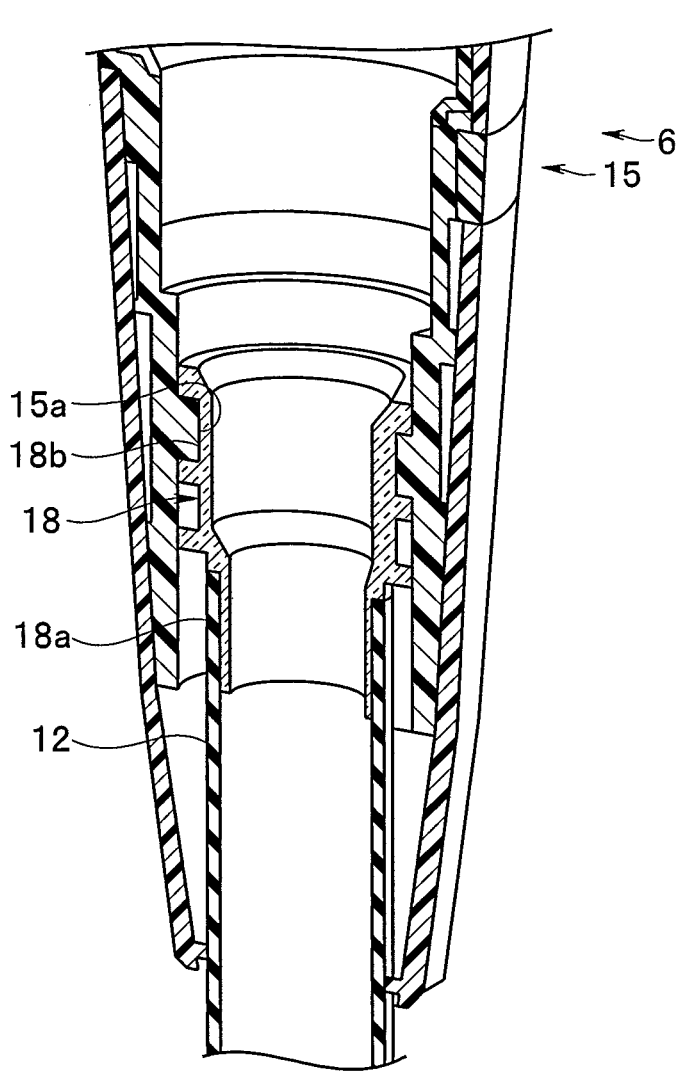
FIG. 4 is a cross-sectional view according to the first embodiment, and shows a distal end side of the operation section.

As shown in FIG. 4, a proximal end side of the flexible tube portion 12 is connected by an adapter 18 to a distal end side of the housing 15. The adapter 18 is a molded resin component having a substantially cylindrical shape, for example.

A connection tube portion 18a is formed on a distal end side of the adapter 18. The connection tube portion 18a has an outer diameter that is substantially the same as an inner diameter of the flexible tube portion 12. The connection tube portion 18a is fixed by adhesion to the flexible tube portion 12 in a state of being inserted in the proximal end side of the flexible tube portion 12. In other words, because the endoscope 1 of the present embodiment is a single-use endoscope, large-scale maintenance such as replacement of the flexible tube portion 12 is not necessary. Accordingly, the proximal end side of the flexible tube portion 12 is firmly fixed to the adapter 18 by a simple configuration using an adhesive.

In the present case, ultraviolet curable resin is desirably used as an adhesive in relation to adhesion between the connection tube portion 18a and the flexible tube portion 12, for example. Adhesion using the ultraviolet curable resin can be implemented by using the adapter 18 that is molded using a transparent resin material having light transmission properties, for example.

Furthermore, a fitting groove 18b is provided on an outer periphery on the proximal end side of the adapter 18. The fitting groove 18b can be fitted with a flange 15a that is formed on an inside of a distal end side of each of the first housing member 16 and the second housing member 17. When the flanges 15a and the fitting groove 18b are fitted, the proximal end side of the flexible tube portion 12 is connected to the housing 15 via the adapter 18.

By using such an adapter 18, a plurality of types of insertion sections 5 (flexible tube portions 12) can be selectively connected to the housing 15 without greatly changing a design of the housing 15 and the like. In other words, a plurality of types of insertion sections 5 can be selectively connected to the housing 15 of the present embodiment simply by making a subtle change in a design such as an outer diameter of the connection tube portion 18a of the adapter 18.

A grasping portion 20 that is used by a surgeon to grasp the operation section 6 by hand is formed at substantially center of the housing 15 in a longitudinal axis O2 direction. A pipe sleeve 21 for inserting a treatment instrument is attached to the housing 15, on a distal end side from the grasping portion 20. Furthermore, on a proximal end side from the grasping portion 20, the housing 15 is provided with an up-down bending operation knob 22 and a left-right bending operation knob 23 as bending operation controllers, a raising base operation lever 24, a gas/liquid feeding button 25, a suction button 26, and a plurality of button switches 27.

Figure 3:
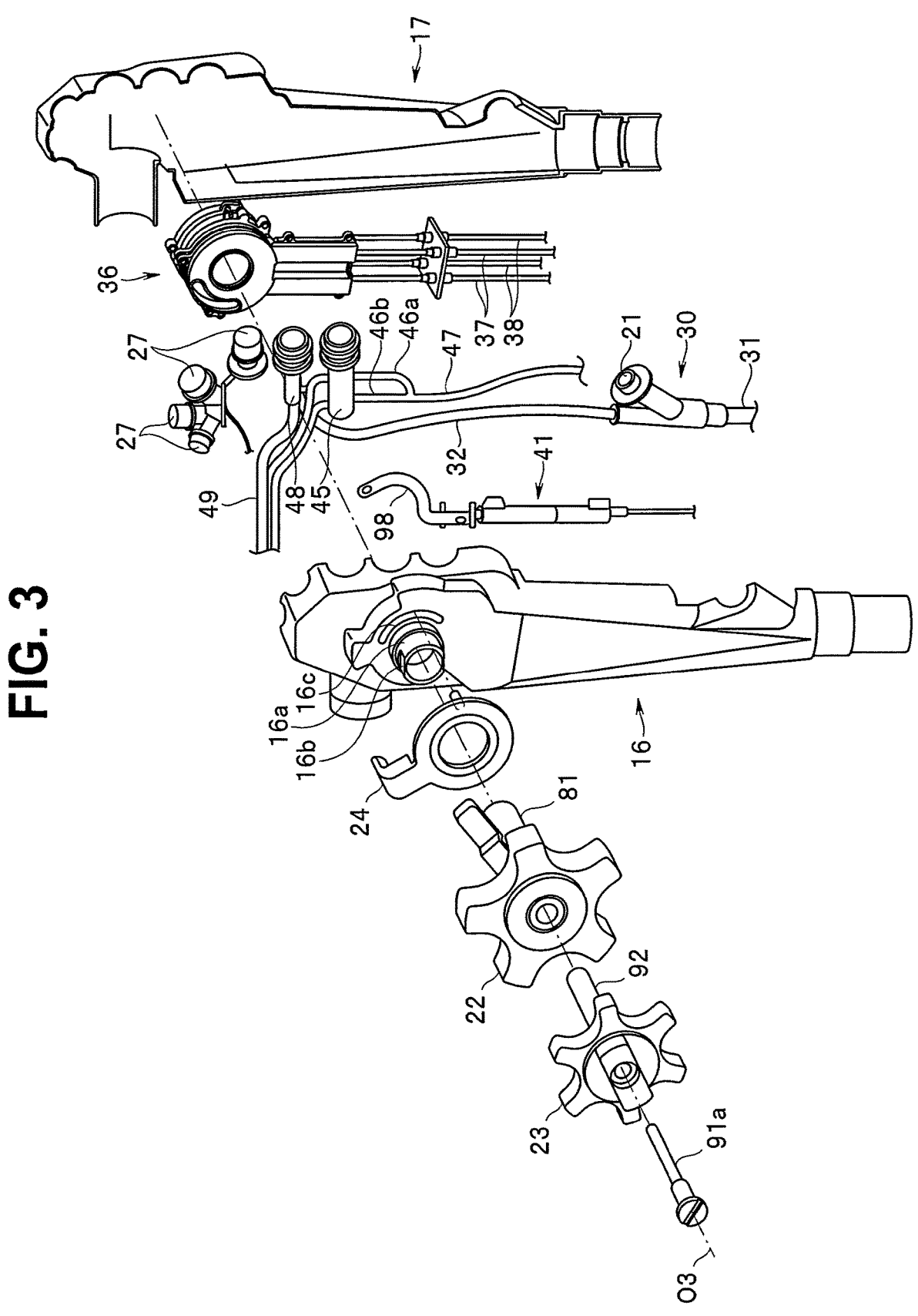
FIG. 3 is an exploded perspective view according to the first embodiment, and shows an operation section.
Figure 5:
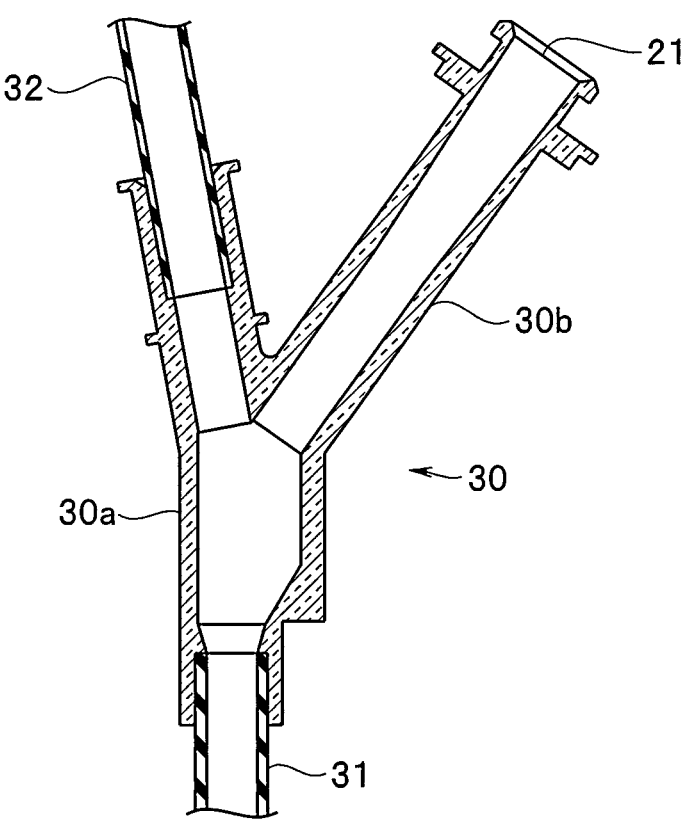
FIG. 5 is a cross-sectional view according to the first embodiment, and shows a branch tube.

As shown in FIGS. 1 and 3, the pipe sleeve 21 is held by the housing 15 in a state of being sandwiched between the first housing member 16 and the second housing member 17. As shown in FIG. 5, the pipe sleeve 21 of the present embodiment is formed at a part of a branch tube 30 that is made of resin and that is disposed inside the housing 15.

The branch tube 30 includes a first conduit 30a that extends in the longitudinal axis O2 direction of the housing 15 (operation section 6), and a second conduit 30b that branches from a middle part of the first conduit 30a in a direction that intersects the longitudinal axis O2. The pipe sleeve 21 is formed at an end portion of the second conduit 30b.

A proximal end side of the treatment instrument channel 31 inserted in the insertion section 5 is connected to an end portion on a distal end side of the first conduit 30a. The treatment instrument channel 31 is fixed by adhesion to the first conduit 30a in a state of being inserted inside the distal end side of the first conduit 30a. The pipe sleeve 21 thereby communicates with the opening portion 10b of the distal end portion 10 via the treatment instrument channel 31.

Furthermore, a distal end side of a first suction tube 32 is connected to an end portion on a proximal end side of the first conduit 30a. The first suction tube 32 is fixed by adhesion to the first conduit 30a in a state of being inserted inside the proximal end side of the first conduit 30a. The first suction tube 32 thus communicates with the opening portion 10b of the distal end portion 10 via the treatment instrument channel 31.

In other words, because the endoscope 1 of the present embodiment is a single-use endoscope, large-scale maintenance such as replacement of the treatment instrument channel 31 and the first suction tube 32 is not necessary. Accordingly, the treatment instrument channel 31 and the first suction tube 32 are firmly fixed to the branch tube 30 by a simple configuration using an adhesive.

In the present case, ultraviolet curable resin is desirably used as an adhesive in relation to adhesion between the branch tube 30 and each of the treatment instrument channel 31 and the first suction tube 32, for example. Adhesion using the ultraviolet curable resin can be implemented by using the branch tube 30 that is molded using a transparent resin material having light transmission properties, for example.

The up-down bending operation knob 22 and the left-right bending operation knob 23 are turnably attached to a side portion of the first housing member 16 while being overlapped on a same center axis O3. The up-down bending operation knob 22 and the left-right bending operation knob 23 form an endoscope bending operation mechanism (hereinafter referred to as a "bending operation mechanism") 35, together with a pulley unit 36 described later. The bending operation mechanism 35 pulls or loosens the up-down bending operation wires 37 and the left-right bending operation wires 38 according to amounts of operation on the up-down bending operation knob 22 and the left-right bending operation knob 23. The bending operation mechanism 35 is thus able to bend the bending portion 11 in every direction including up-down and left-right directions.

The raising base operation lever 24 is turnably attached to the side portion of the first housing member 16, between the up-down bending operation knob 22 and the first housing member 16. The raising base operation lever 24 forms a raising base operation mechanism 40, together with a cylinder unit 41 described later. The raising base operation mechanism 40 pulls or loosens the raising base operation wire 42 according to an amount of operation on the raising base operation lever 24. The raising base operation mechanism 40 can thereby cause the raising base 10c to swing.

The gas/liquid feeding button 25 is an operation button for feeding gas and liquid from the nozzle 10f to the flat portion 10a of the distal end portion 10. The gas/liquid feeding button 25 is attached to the housing 15 via a gas/liquid feeding cylinder 45 made of resin.

Figure 6:
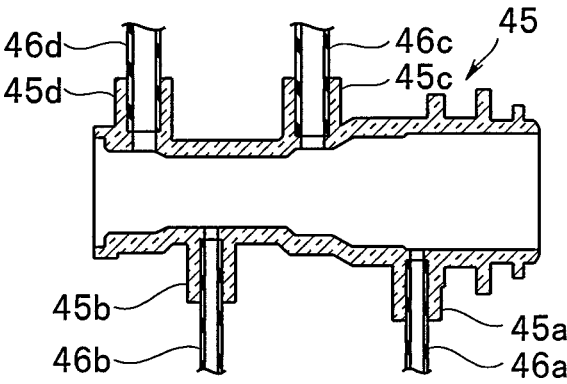
FIG. 6 is a cross-sectional view according to the first embodiment, and shows a gas/liquid feeding cylinder.

As shown in FIG. 6, the gas/liquid feeding cylinder 45 includes a first gas feeding port 45a, a first liquid feeding port 45b, a second gas feeding port 45c, and a second liquid feeding port 45d. A piston, not shown, that is connected to the gas/liquid feeding button 25 is provided inside the gas/liquid feeding cylinder 45. The piston moves forward and backward inside the gas/liquid feeding cylinder 45 according to a pressed state of the gas/liquid feeding button 25. The piston causes the first gas feeding port 45a and the second gas feeding port 45c to communicate with each other or to be shut off from each other, and causes the first liquid feeding port 45b and the second liquid feeding port 45d to communicate with each other or to be shut off from each other, depending on a forward/backward position inside the gas/liquid feeding cylinder 45.

An end portion on a proximal end side of a first gas feeding tube 46a is connected to the first gas feeding port 45a. The first gas feeding tube 46a is fixed by adhesion to the first gas feeding port 45a in a state of being inserted inside the first gas feeding port 45a.

An end portion on a proximal end side of a first liquid feeding tube 46b is connected to the first liquid feeding port 45b. The first liquid feeding tube 46b is fixed by adhesion to the first liquid feeding port 45b in a state of being inserted inside the first liquid feeding port 45b.

Here, as shown in FIG. 3, end portions on distal end sides of the first gas feeding tube 46a and the first liquid feeding tube 46b both communicate with an end portion on a proximal end side of the gas/liquid feeding tube 47.

Furthermore, an end portion on a distal end side of a second gas feeding tube 46c is connected to the second gas feeding port 45c. The second gas feeding tube 46c is fixed by adhesion to the second gas feeding port 45c in a state of being inserted inside the second gas feeding port 45c.

Furthermore, an end portion on a distal end side of a second liquid feeding tube 46d is connected to the second liquid feeding port 45d. The second liquid feeding tube 46d is fixed by adhesion to the second liquid feeding port 45d in a state of being inserted inside the second liquid feeding port 45d.

In other words, because the endoscope 1 of the present embodiment is a single-use endoscope, large-scale maintenance such as replacement of each gas feeding tube and each liquid feeding tube is not necessary. Accordingly, each tube is firmly fixed to the gas/liquid feeding cylinder 45 by a simple configuration using an adhesive.

In the present case, ultraviolet curable resin is desirably used as an adhesive in relation to adhesion between the first gas feeding port 45a and the first gas feeding tube 46a, adhesion between the first liquid feeding port 45b and the first liquid feeding tube 46b, adhesion between the second gas feeding port 45c and the second gas feeding tube 46c, and adhesion between the second liquid feeding port 45d and the second liquid feeding tube 46d, for example. Adhesion using the ultraviolet curable resin can be implemented by using the gas/liquid feeding cylinder 45 that is molded using a transparent resin material having light transmission properties, for example.

The suction button 26 is an operation button for performing suction of liquid or a solid matter from the opening portion 10b provided in the distal end portion 10. The suction button 26 is attached to the housing 15 via a suction cylinder 48 that is made of resin.

Figure 7:
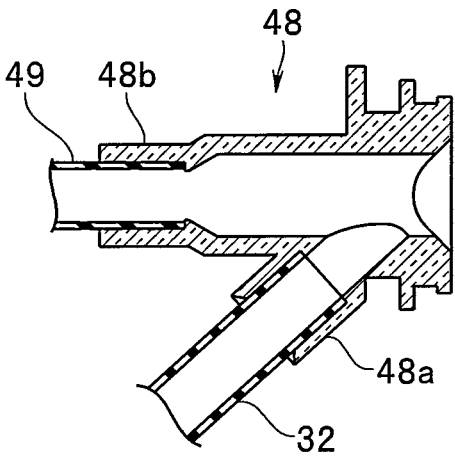
FIG. 7 is a cross-sectional view according to the first embodiment, and shows a suction cylinder.

As shown in FIG. 7, the suction cylinder 48 includes a first suction port 48a and a second suction port 48b. A piston, not shown, is provided inside the suction cylinder 48. The piston moves forward and backward inside the suction cylinder 48 according to a pressed state of the suction button 26. The piston causes the first suction port 48a and the second suction port 48b to communicate with each other or to be shut off from each other, depending on a forward/backward position inside the suction cylinder 48.

An end portion on a proximal end side of the first suction tube 32 is connected to the first suction port 48a. The first suction tube 32 is fixed by adhesion to the first suction port 48a in a state of being inserted inside the first suction port 48a.

Furthermore, an end portion on a distal end side of a second suction tube 49 is connected to the second suction port 48b. The second suction tube 49 is fixed by adhesion to the second suction port 48b in a state of being inserted inside the second suction port 48b.

In other words, because the endoscope 1 of the present embodiment is a single-use endoscope, large-scale maintenance such as replacement of each suction tube is not necessary. Accordingly, each tube is firmly fixed to the suction cylinder 48 by a simple configuration using an adhesive.

In the present case, ultraviolet curable resin is desirably used as an adhesive in relation to adhesion between the first suction port 48*a* and the first suction tube 32, and adhesion between the second suction port 48*b* and the second suction tube 49, for example. Adhesion using the ultraviolet curable resin can be implemented by using the suction cylinder 48 that is molded using a transparent resin material having light transmission properties, for example.

A plurality of button switches 27 are held by the housing 15 in a state of being sandwiched between the first housing member 16 and the second housing member 17. The button switches 27 can be assigned as switches for implementing various functions of the endoscope 1.

The universal cord 7 extends from a proximal end side of the operation section 6. Tubes and the like including the second gas feeding tube 46*c*, the second liquid feeding tube 46*d*, and the second suction tube 49 are inserted inside the universal cord 7. Furthermore, various signal cables connected to each button switch, the image pickup device of the image pickup unit, and the like are inserted inside the universal cord 7. Moreover, a light guide bundle that is optically connected to the illumination optical system, and the like are inserted inside the universal cord 7.

The endoscope connector 8 is connected to an extended end portion of the universal cord 7. The endoscope connector 8 can be connected via a relay connector 9 to an external appliance (not shown) such as a light source device or a processor.

As shown in FIG. 1, the endoscope connector 8 of the present embodiment has a substantially quadrangular prism shape, for example. The endoscope connector 8 includes, on a side surface, a liquid feeding connector 8*a* to be connected to the second liquid feeding tube 46*d*, and a suction connector 8*b* to be connected to the second suction tube 49, for example. Furthermore, the endoscope connector 8 includes, on a side surface, an engaging claw 8*c* that can be engaged with the relay connector 9. Moreover, the endoscope connector 8 includes, on an end surface, a gas feeding plug to be connected to the second gas feeding tube 46*c*, a plurality of electrical connectors to be connected to various signal cables, and a light guide connector to be connected to the light guide bundle (none of which is shown).

The relay connector 9 is a reusable product that can be used several times. In other words, the relay connector 9 can be repeatedly used on a plurality of endoscopes 1 (single-use endoscopes). The relay connector 9 has a substantially round columnar shape, for example.

The relay connector 9 includes a control board 9*a* inside. The control board 9*a* performs various types of signal processing on the image pickup signal, correction processing on power current supplied to the endoscope 1, and the like.

Furthermore, the relay connector 9 includes, on a distal end surface, a light source connector 9*b* and a gas feeding plug 9*c*. Moreover, the relay connector 9 includes a plurality of electric contacts 9*d* on a side surface.

Moreover, a connector receiving hole 9*e* where the endoscope connector 8 can be inserted is provided in a proximal end portion of the relay connector 9. The connector receiving hole 9*e* has a substantially rectangular hole shape, for example. A proximal end side of the light source connector 9*b* protrudes inside the connector receiving hole 9*e*. The proximal end side of the light source connector 9*b* is disposed at a position that allows optical connection with the light guide connector of the endoscope connector 8. A gas feeding pipe sleeve to be connected to the gas feeding plug 9*c*, and an electrical connector receiver to be connected to each electric contact 9*d* are provided inside the connector receiving hole 9*e* (none of which is shown). Of the above, the gas feeding pipe sleeve is provided at a position that allows connection with the gas feeding plug of the endoscope connector 8. Furthermore, the electrical connector receiver is provided at a position that allows connection with an electrical connector of the endoscope connector 8.

Next, a configuration of the bending operation mechanism 35 will be described in detail.

Figure 8:
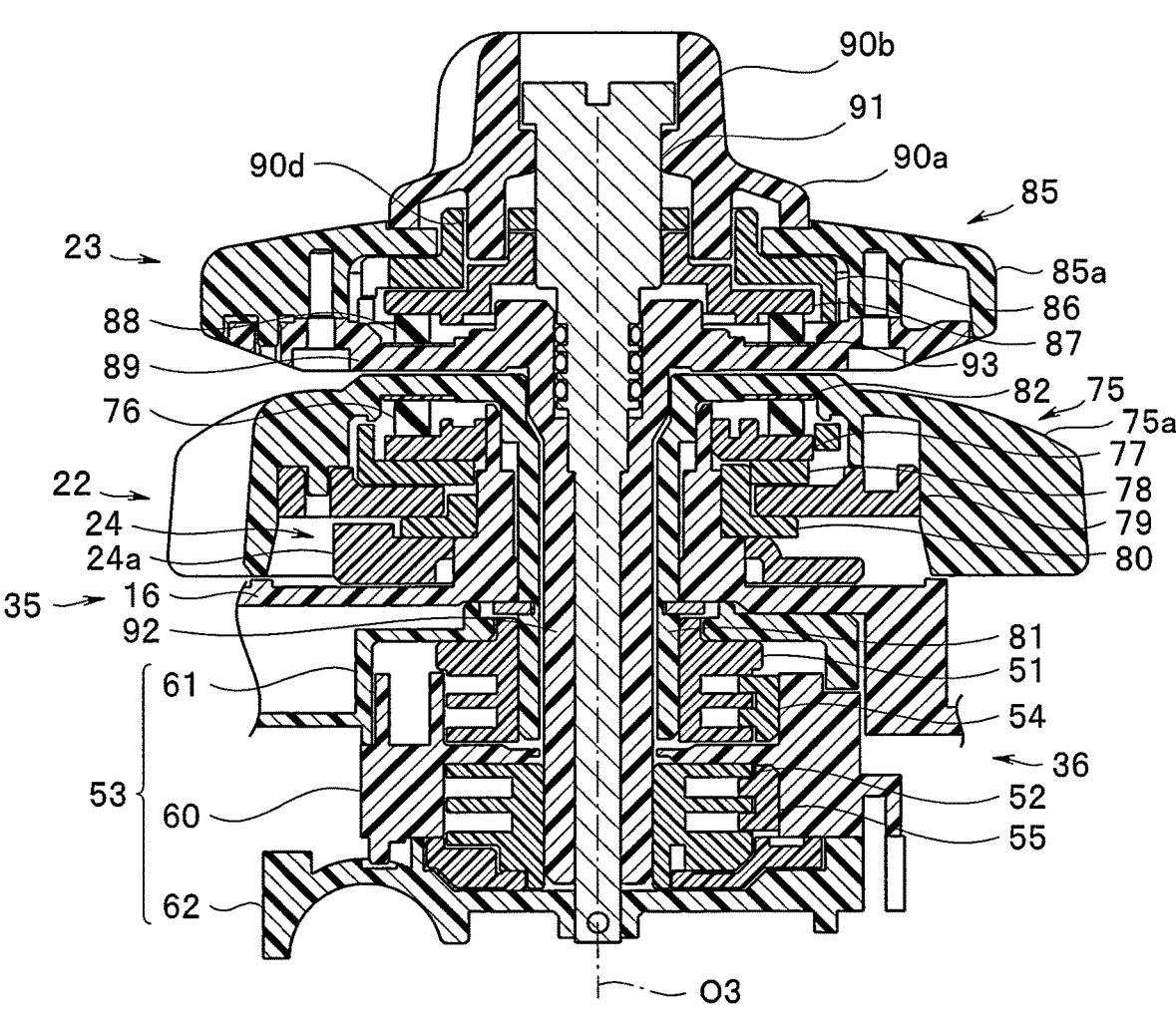
FIG. 8 is a cross-sectional view according to the first embodiment, and shows main parts of a bending operation mechanism.
Figure 9:
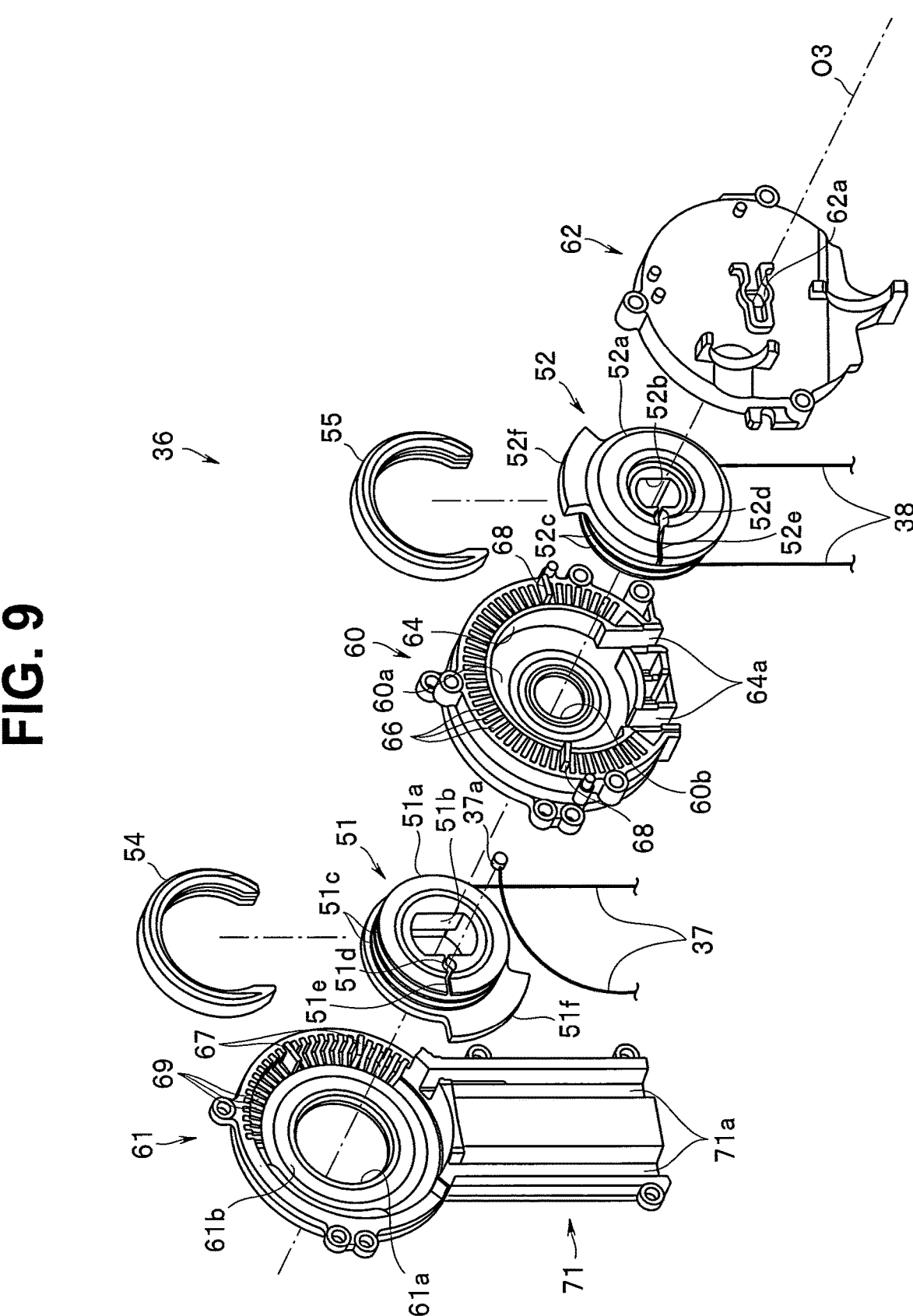
FIG. 9 is an exploded perspective view according to the first embodiment, and shows a bending operation mechanism main body from one end side.
Figure 10:
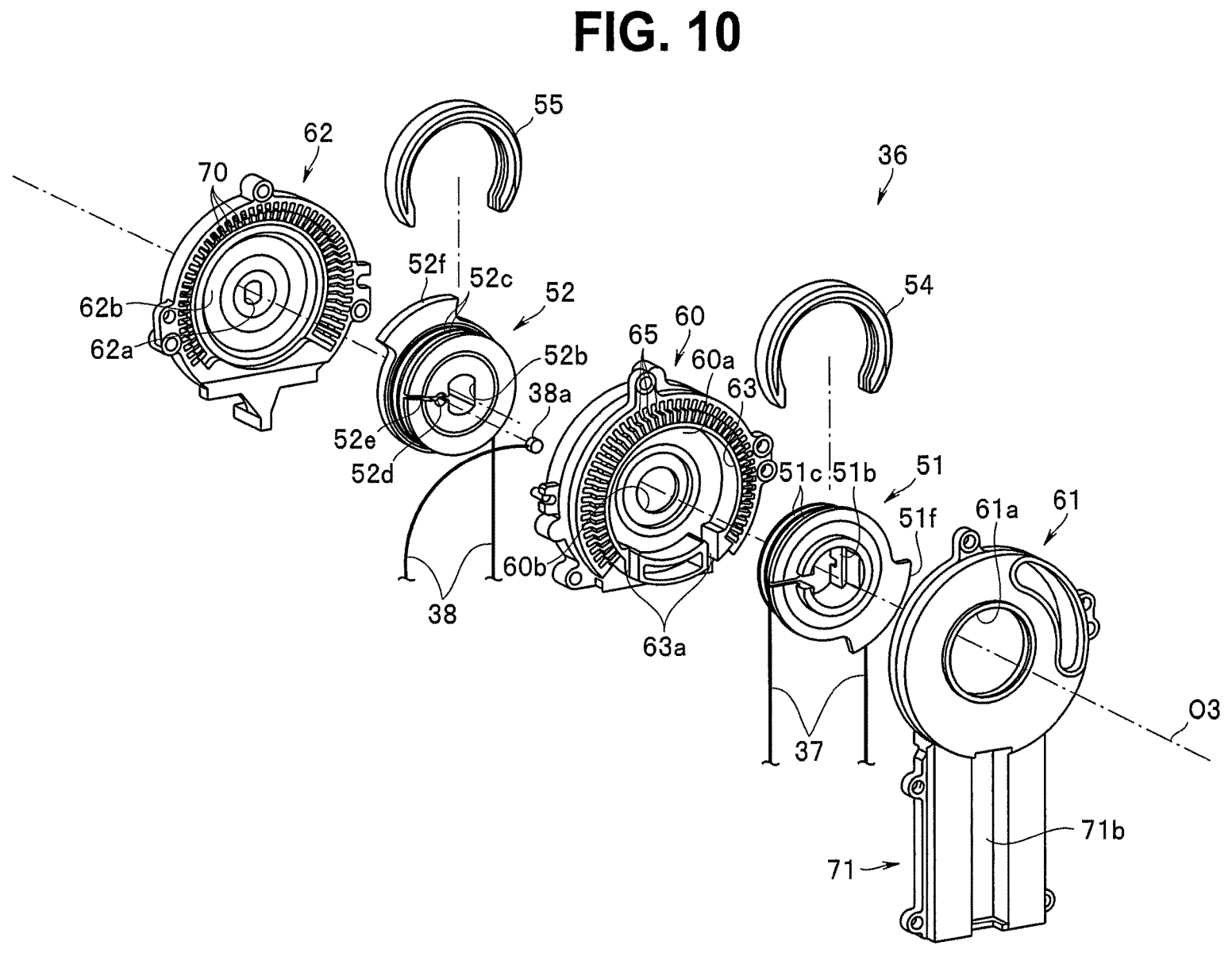
Figure 11:
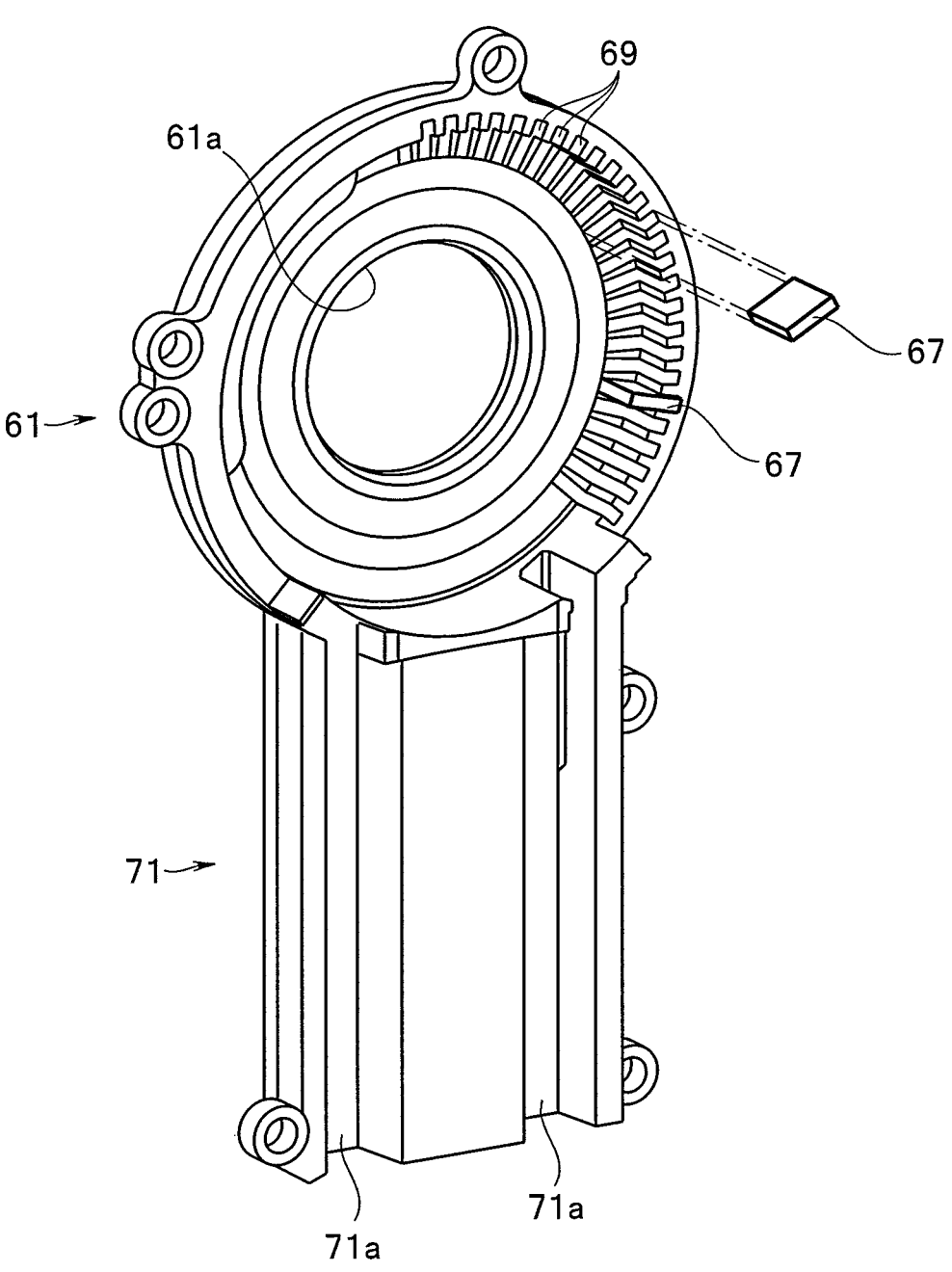
FIG. 11 is a perspective view according to the first embodiment, and shows a first case member in an enlarged manner.

As shown in FIGS. 8 to 10, the pulley unit 36 of the bending operation mechanism 35 includes an up-down bending pulley 51 and a left-right bending pulley 52 as turning members, and a pulley case 53 as a holding member. Nota that, in the description of the bending operation mechanism 35 given below, a side of the left-right bending pulley 52 relative to the up-down bending pulley 51 in a center axis O3 direction of the bending operation mechanism 35 is taken as one end (one side), and a side of the up-down bending pulley 51 relative to the left-right bending pulley 52 in the center axis O3 direction of the bending operation mechanism 35 is taken as the other end (the other side).

The up-down bending pulley 51 includes an up-down bending pulley main body 51*a* that is disk-shaped (drum-shaped) and that has a predetermined thickness.

A keyhole 51*b* that penetrates in the center axis O3 direction is provided at a center part of the up-down bending pulley main body 51*a*.

Furthermore, a pair of pulley grooves 51*c* are provided on an outer peripheral portion of the up-down bending pulley main body 51*a*.

Furthermore, wire stop receiving holes 51*d* are provided respectively on both side portions of the up-down bending pulley main body 51*a* (both side portions of the up-down bending pulley main body 51*a* in the center axis O3 direction). Moreover, connection grooves 51*e* are provided on both side portions of the up-down bending pulley main body 51*a* to connect the wire stop receiving holes 51*d* to the respective pulley grooves 51*c*.

Furthermore, a protruding portion (stopper structure) 51*f* as an abutting portion is provided on the other side portion of the up-down bending pulley main body 51*a*. In the present embodiment, the protruding portion 51*f* has a partial arc shape, for example, and protrudes in an outer diameter direction of the up-down bending pulley main body 51*a*.

Proximal end sides of the pair of up-down bending operation wires 37 can each be wound around the up-down bending pulley 51 structured in the above manner. In the present case, a wire stop 37*a* attached to a proximal end portion of the up-down bending operation wire 37 is inserted in respective wire stop receiving hole 51*d*. Each up-down bending operation wire 37 is thereby coupled to the up-down bending pulley 51. The up-down bending operation wires 37 are thus guided to the respective pulley grooves 51*c* via the respective connection grooves 51*e*.

Note that a protection member 54 that forms a partial arc is mounted on a part of an outer periphery of the up-down bending pulley 51. The protection member 54 covers a part of each pulley groove 51*c*. The up-down bending operation wires 37 are thus prevented from falling out of the respective pulley grooves 51*c*.

The left-right bending pulley 52 includes a left-right bending pulley main body 52*a* that is disk-shaped (drum-shaped) and that has a predetermined thickness.

A keyhole 52*b* that penetrates in the center axis O3 direction is provided at a center part of the left-right bending pulley main body 52*a*.

Furthermore, a pair of pulley grooves 52*c* are provided on an outer peripheral portion of the left-right bending pulley main body 52*a*.

Furthermore, wire stop receiving holes 52*d* are provided respectively on both side portions of the left-right bending pulley main body 52*a*. Moreover, connection grooves 52*e* are provided on both side portions of the left-right bending pulley main body 52*a* to connect the wire stop receiving holes 52*d* to the respective pulley grooves 52*c*.

Furthermore, a protruding portion 52*f* as an abutting portion is provided on one side portion of the left-right bending pulley main body 52*a*. In the present embodiment, the protruding portion 52*f* has a partial arc shape, for example, and protrudes in an outer diameter direction of the left-right bending pulley main body 52*a*.

Proximal end sides of the pair of left-right bending operation wires 38 can each be wound around the left-right bending pulley 52 structured in the above manner. In the present case, a wire stop 38*a* attached to a proximal end portion of the left-right bending operation wire 38 is inserted in each wire stop receiving hole 52*d*. Each left-right bending operation wire 38 is thereby coupled to the left-right bending pulley 52. The left-right bending operation wires 38 are thus guided to the respective pulley grooves 52*c* via the respective connection grooves 52*e*.

Note that a protection member 55 that forms a partial arc is mounted on a part of an outer periphery of the left-right bending pulley 52. The protection member 55 covers a part of each pulley groove 52*c*. The left-right bending operation wires 38 are thus prevented from falling out of the respective pulley grooves 52*c*.

The pulley case 53 includes a case main body 60, and a first case member 61 and a second case member 62 that are attached to both sides of the case main body 60. Here, in the present embodiment, the case main body 60 corresponds to a specific example of a first holding member, the first case member 61 corresponds to a specific example of a second holding member, and the second case member 62 corresponds to a specific example of a third holding member.

The case main body 60 is formed by a member having a substantially cylindrical shape. An inner diameter of the case main body 60 is greater than an outer diameter of each protection member 54, 55, and smaller than an outer diameter of each protruding portion 51*f*, 52*f* forming an arc.

Furthermore, a partition wall 60*a* is provided inside the case main body 60. Inside of the case main body 60 is divided into an up-down bending pulley chamber 63 and a left-right bending pulley chamber 64 by the partition wall 60*a*. Moreover, a shaft hole 60*b* that penetrates in the center axis O3 direction is provided at a center part of the partition wall 60*a*.

A depth of the up-down bending pulley chamber 63 (a depth in the center axis O3 direction) is set to be smaller by a predetermined amount than a thickness of the up-down bending pulley 51. The up-down bending pulley chamber 63 is thereby capable of housing the up-down bending pulley 51 with the protruding portion 51*f* facing the other end surface of the case main body 60.

Furthermore, a pair of communication grooves 63*a* for allowing inside of the up-down bending pulley chamber 63 to communicate with outside are provided in the case main body 60. The up-down bending operation wires 37 wound around the respective pulley grooves 51*c* of the up-down bending pulley 51 are thus allowed by the communication grooves 63*a* to extend outside the up-down bending pulley chamber 63.

Moreover, a plurality of mounting portions (mounting section) 65 are provided on the other end surface of the case main body 60 in the center axis O3 direction. The mounting portions 65 are formed as slit-shaped recessed grooves, for example. The mounting portions 65 are radially arranged around the center axis O3 of the case main body 60 with predetermined gaps. A stopper member (limit structure) 67 that is a flat plate made of metal can be removably mounted in each mounting portion 65, for example. The stopper member 67 and the protruding portion 51*f* can form a movement limiter unit. The movement limiter unit can limit the movement mechanically, electronically, or magnetically.

Figure 12:
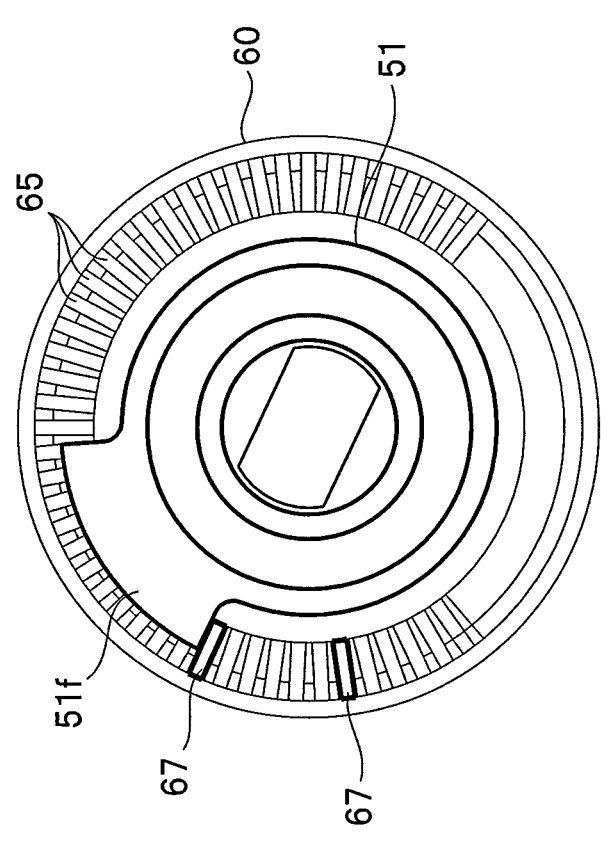
FIG. 12 is a plan view according to the first embodiment, and schematically shows a state where an up-down bending pulley is turned to a first turning end position.
Figure 13:
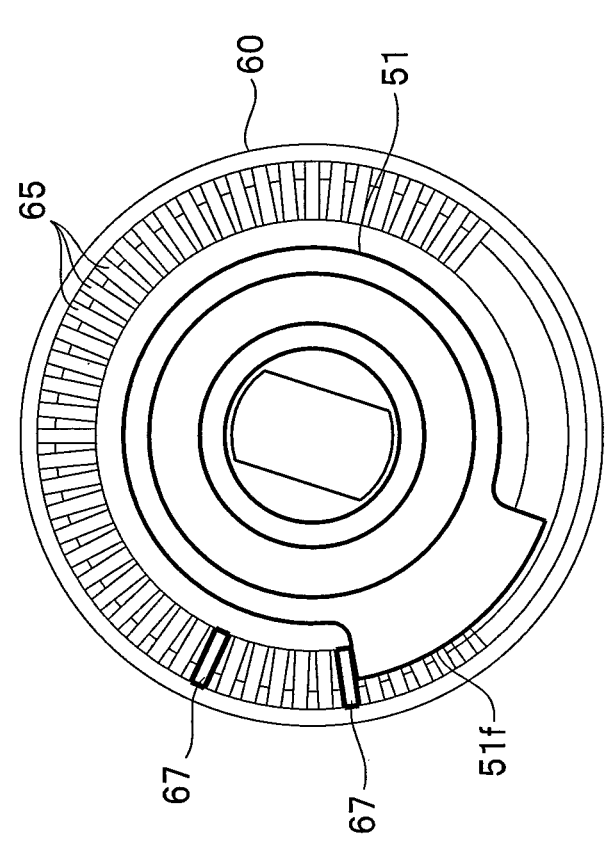
FIG. 13 is a plan view according to the first embodiment, and schematically shows a state where the up-down bending pulley is turned to a second turning end position.
Figure 14:
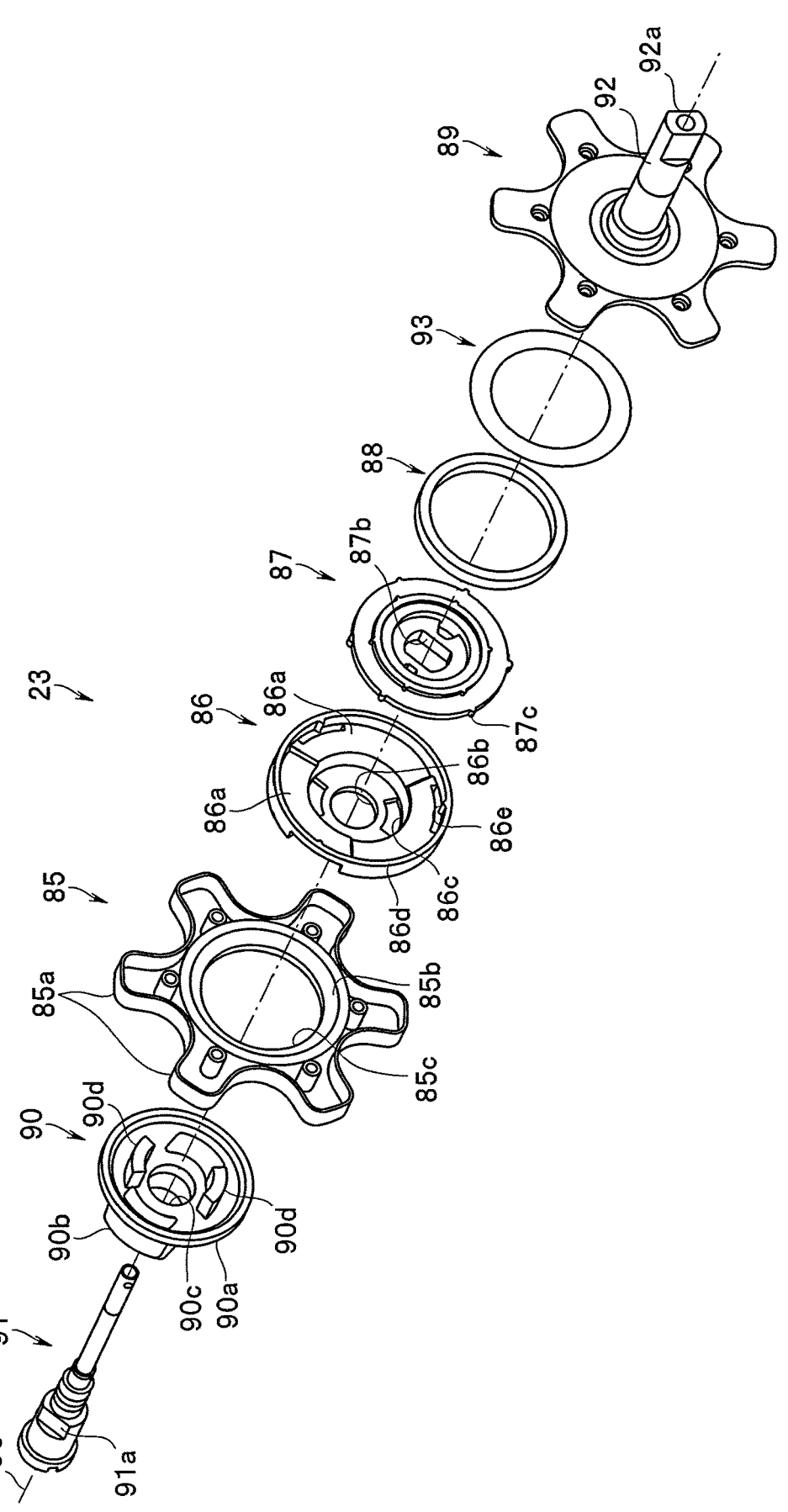
FIG. 14 is an exploded perspective view according to the first embodiment, and shows a left-right bending operation knob from one end side.
Figure 15:
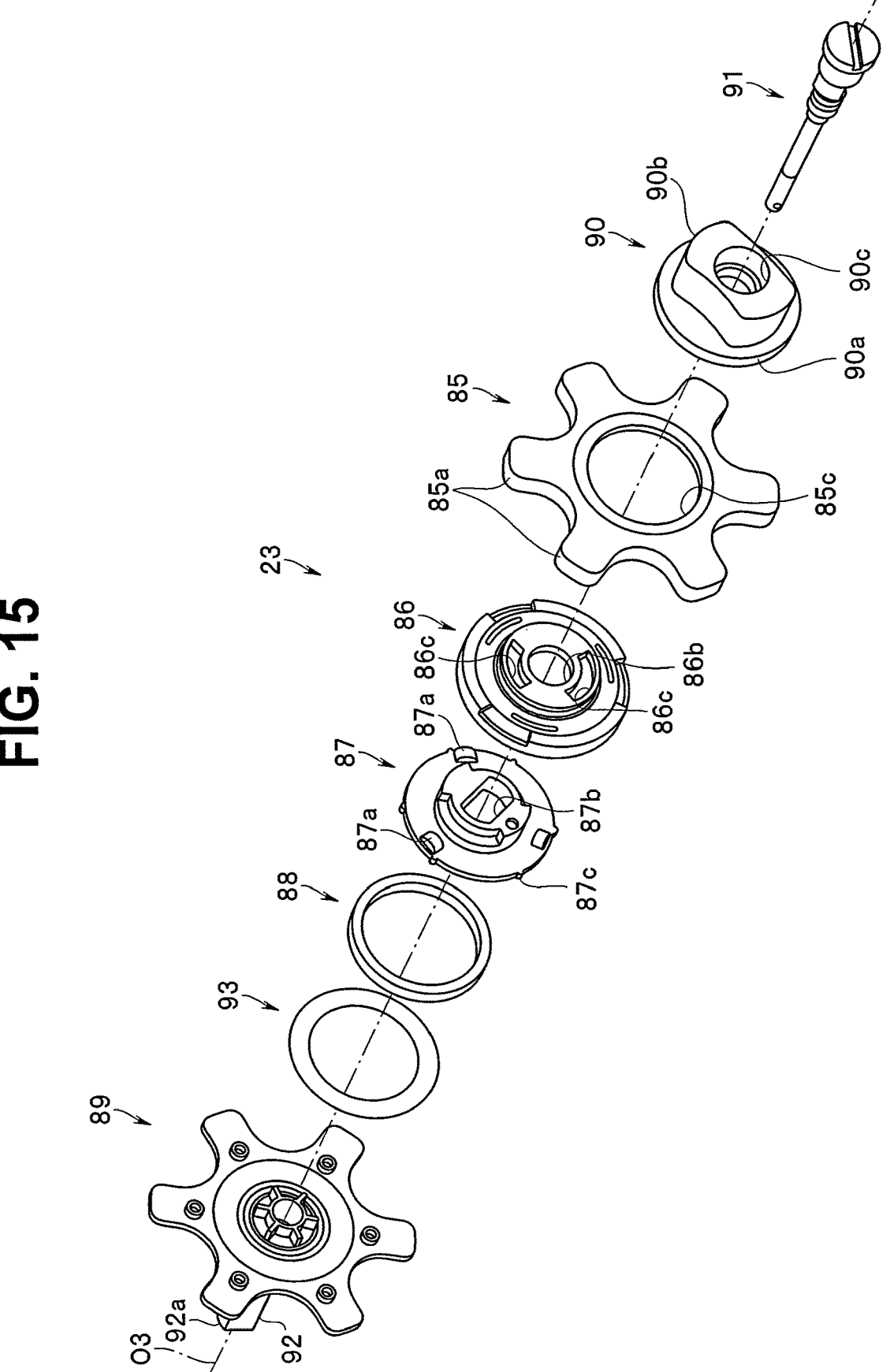
FIG. 15 is an exploded perspective view according to the first embodiment, and shows the left-right bending operation knob from the other end side.
Figure 17:
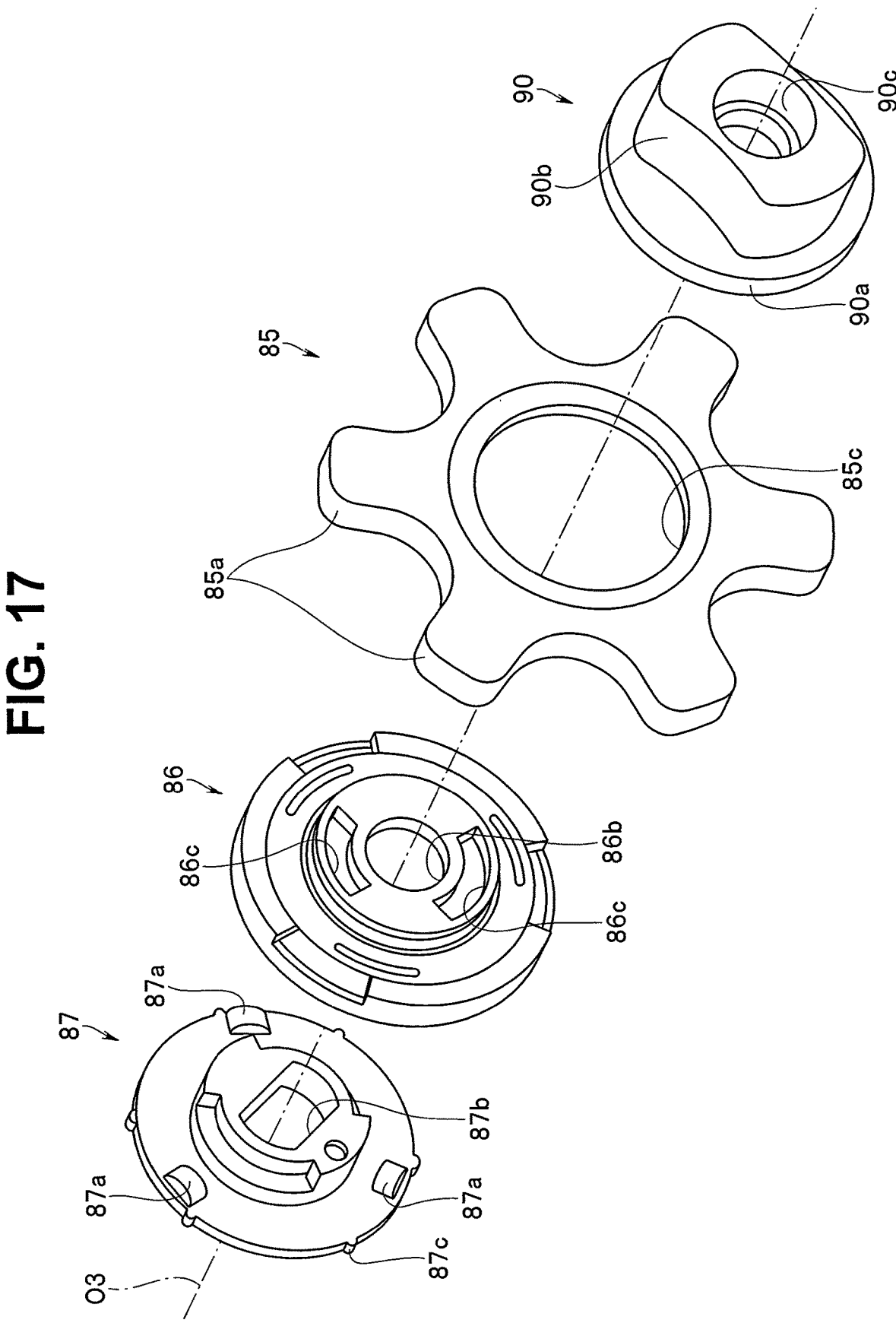
FIG. 17 is an exploded perspective view according to the first embodiment, and shows the main parts of the left-right bending operation knob in an enlarged manner from the other end side.
Figure 18:
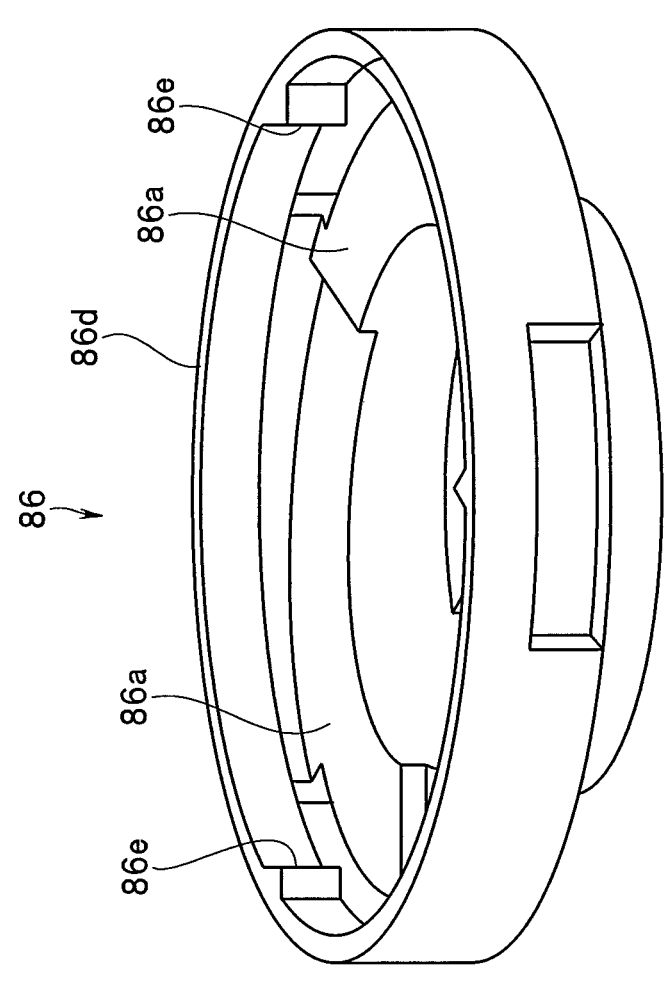
FIG. 18 is a perspective view according to the first embodiment, and shows a cam plate in an enlarged manner.
Figure 19:
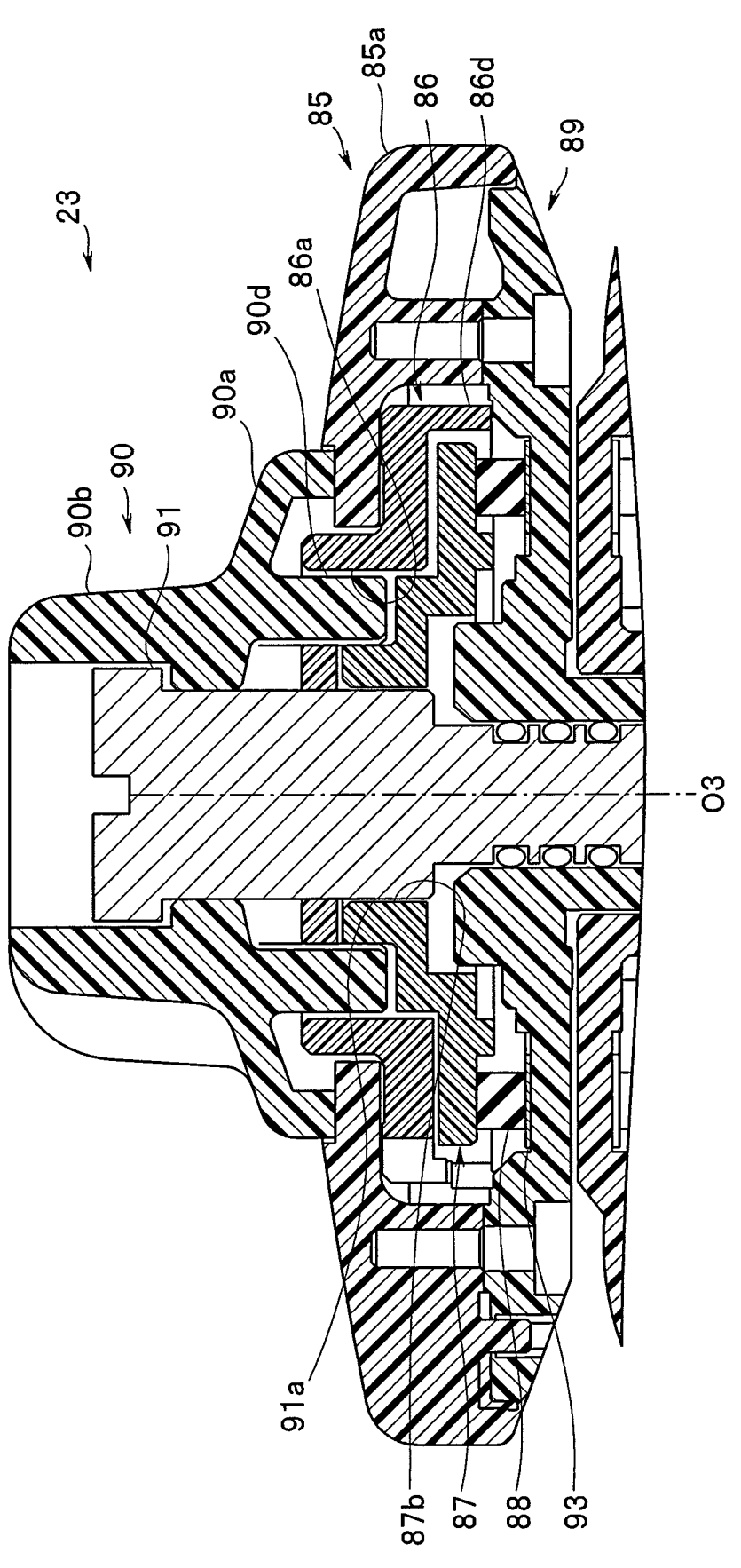
FIG. 19 is a cross-sectional view according to the first embodiment, and shows main parts of the left-right bending operation knob when a brake is released.
Figure 20:
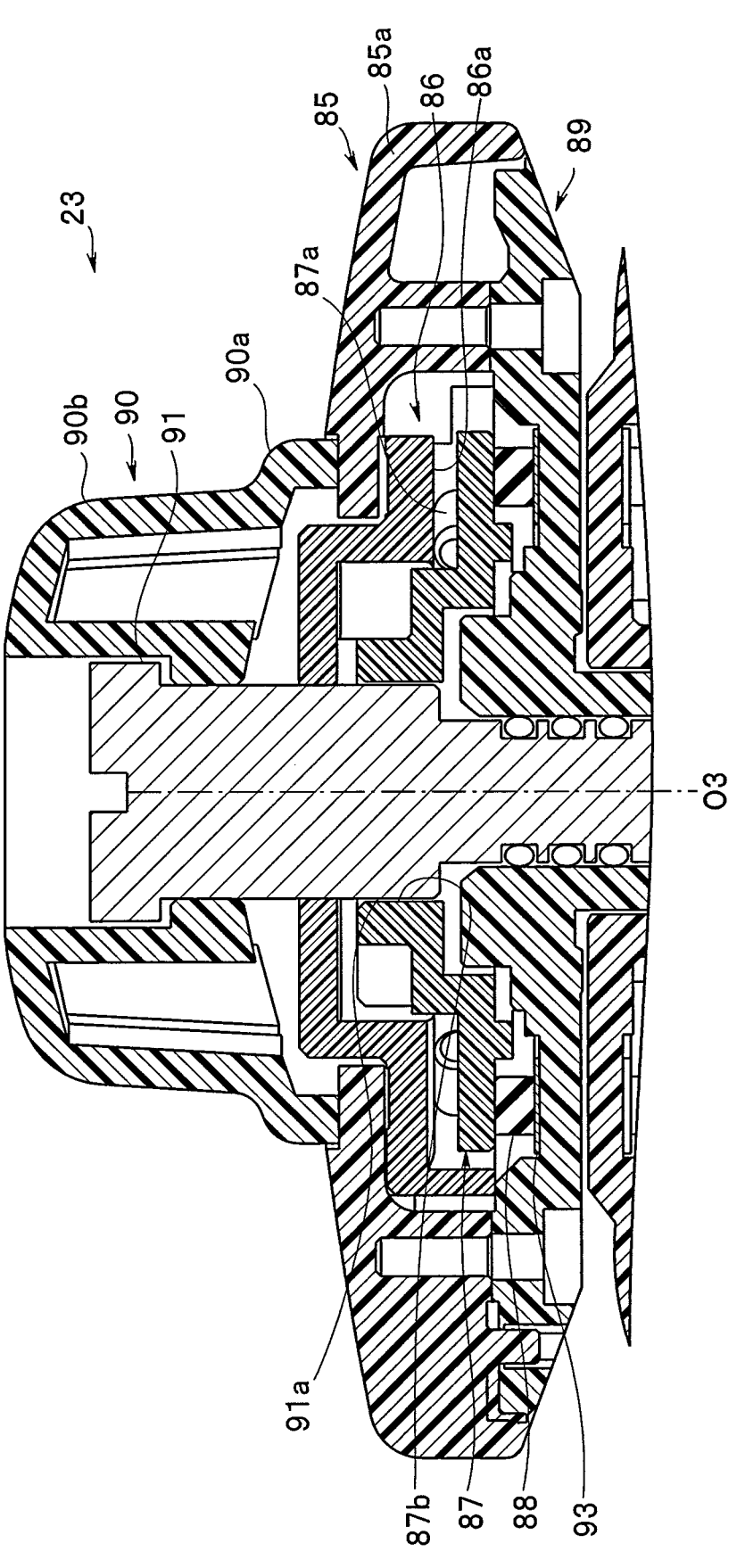
FIG. 20 is a cross-sectional view according to the first embodiment, and shows the main parts of the left-right bending operation knob when the brake is operated.

At least one stopper member 67 is selectively mounted in a group of mounting portions 65 that are arranged in the above manner. In the present embodiment, two stopper members 67 are selectively mounted in the group of mounting portions 65. A part of the stopper member 67 mounted in the mounting portion 65 protrudes from the other end surface of the case main body 60. A protruding part of the stopper member 67 can contact the protruding portion 51*f* of the up-down bending pulley 51. Each stopper member 67 thus restricts a rotation angle of the up-down bending pulley 51. In other words, each stopper member 67 defines a rotation angle region of the up-down bending pulley 51 according to a position of the mounting portion 65 to which the stopper member 67 is selectively attached (for example, see FIGS. 12 and 13).

A depth of the left-right bending pulley chamber 64 (a depth in the center axis O3 direction) is set to be smaller by a predetermined amount than a thickness of the left-right bending pulley 52. The left-right bending pulley chamber 64 is thereby capable of housing the left-right bending pulley 52 with the protruding portion 52*f* facing one end surface of the case main body 60.

Furthermore, a pair of communication grooves 64*a* for allowing inside of the left-right bending pulley chamber 64 to communicate with outside are provided in the case main body 60. The left-right bending operation wires 38 wound around the respective pulley grooves 52*c* of the left-right bending pulley 52 are thus allowed by the communication grooves 64*a* to extend outside the left-right bending pulley chamber 64.

Moreover, a plurality of mounting portions 66 are provided on the one end surface of the case main body 60 in the center axis O3 direction. The mounting portions 66 are formed as slit-shaped recessed grooves, for example. The mounting portions 66 are radially arranged around the center axis O3 of the case main body 60 with predetermined gaps. A stopper member 68 that is a flat plate made of metal can be removably mounted in each mounting portion 66, for example.

At least one stopper member 68 is selectively mounted in a group of mounting portions 66 that are arranged in the above manner. In the present embodiment, two stopper members 68 are selectively mounted in the group of mounting portions 66. A part of the stopper member 68 mounted in the mounting portion 66 protrudes from the one end surface of the case main body 60. A protruding part of the stopper member 68 can contact the protruding portion 52*f* of the left-right bending pulley 52. Each stopper member 68 thus restricts a rotation angle of the left-right bending pulley 52. In other words, each stopper member 68 defines a rotation angle region of the left-right bending pulley 52 according to a position of the mounting portion 66 to which the stopper member 68 is selectively attached.

The first case member 61 is substantially disk-shaped. The first case member 61 has an outer diameter that is substantially the same as an outer diameter of the case main body 60. Furthermore, a shaft hole 61*a* that penetrates in the center axis O3 direction is provided at a center part of the first case member 61.

A recessed portion 61b for avoiding interference with the protruding portion 51f of the up-down bending pulley 51 is formed in one end surface of the first case member 61 (a surface on a side facing the other end surface of the case main body 60).

Furthermore, a mounting portion 69 corresponding to each mounting portion 65 provided on the other end surface of the case main body 60 is provided on the one end surface of the first case member 61.

The first case member 61 structured in the above manner is fixed to the other end of the case main body 60 by screwing or the like. Due to the fixing, the first case member 61 sandwiches the up-down bending pulley 51 with the case main body 60. The up-down bending pulley 51 is thereby turnably held inside the up-down bending pulley chamber 63.

At the time, the stopper member 67 is held in a state of being sandwiched between the mounting portion 65 and the mounting portion 69. Note that, to simplify the structure, one of the mounting portion 65 on the other end surface of the case main body 60 or the mounting portion 69 of the first case member 61 can be omitted.

Furthermore, a bracket 71 is integrally formed with the first case member 61. The bracket 71 has a substantially rectangular plate shape that extends in an outer diameter direction of the first case member 61.

Moreover, the bracket 71 is provided with groove-shaped guide portions 71a for guiding the pair of up-down bending operation wires 37 extending from the up-down bending pulley chamber 63, and the pair of left-right bending operation wires 38 extending from the left-right bending pulley chamber 64.

The second case member 62 is substantially disk-shaped. The second case member 62 has an outer diameter that is substantially the same as the outer diameter of the case main body 60. Furthermore, a shaft hole 62a that penetrates in the center axis O3 direction is provided at a center part of the second case member 62.

A recessed portion 62b for avoiding interference with the protruding portion 52f of the left-right bending pulley 52 is formed in the other end surface of the second case member 62 (a surface on a side facing the one end surface of the case main body 60).

Furthermore, a mounting portion 70 corresponding to each mounting portion 66 provided on the one end surface of the case main body 60 is provided on the other end surface of the second case member 62.

The second case member 62 structured in the above manner is fixed to one end of the case main body 60 by screwing or the like. Due to the fixing, the second case member 62 sandwiches the left-right bending pulley 52 with the case main body 60. The left-right bending pulley 52 is thereby turnably held inside the left-right bending pulley chamber 64.

At the time, the stopper member 68 is held in a state of being sandwiched between the mounting portion 66 and the mounting portion 70. Note that, to simplify the structure, one of the mounting portion 66 on the one end surface of the case main body 60 or the mounting portion 70 of the second case member 62 can be omitted.

The pulley unit 36 structured in the above manner is fixed to an inner surface side of the first housing member 16 by screwing or the like. More specifically, the pulley unit 36 is fixed to the first housing member 16 by using at least one of a plurality of screws that fix the first case member 61 and the second case member 62 to the case main body 60, for example. Furthermore, the pulley unit 36 is fixed to the first housing member 16 by screwing the bracket 71 to the first housing member 16, for example.

Figure 21:
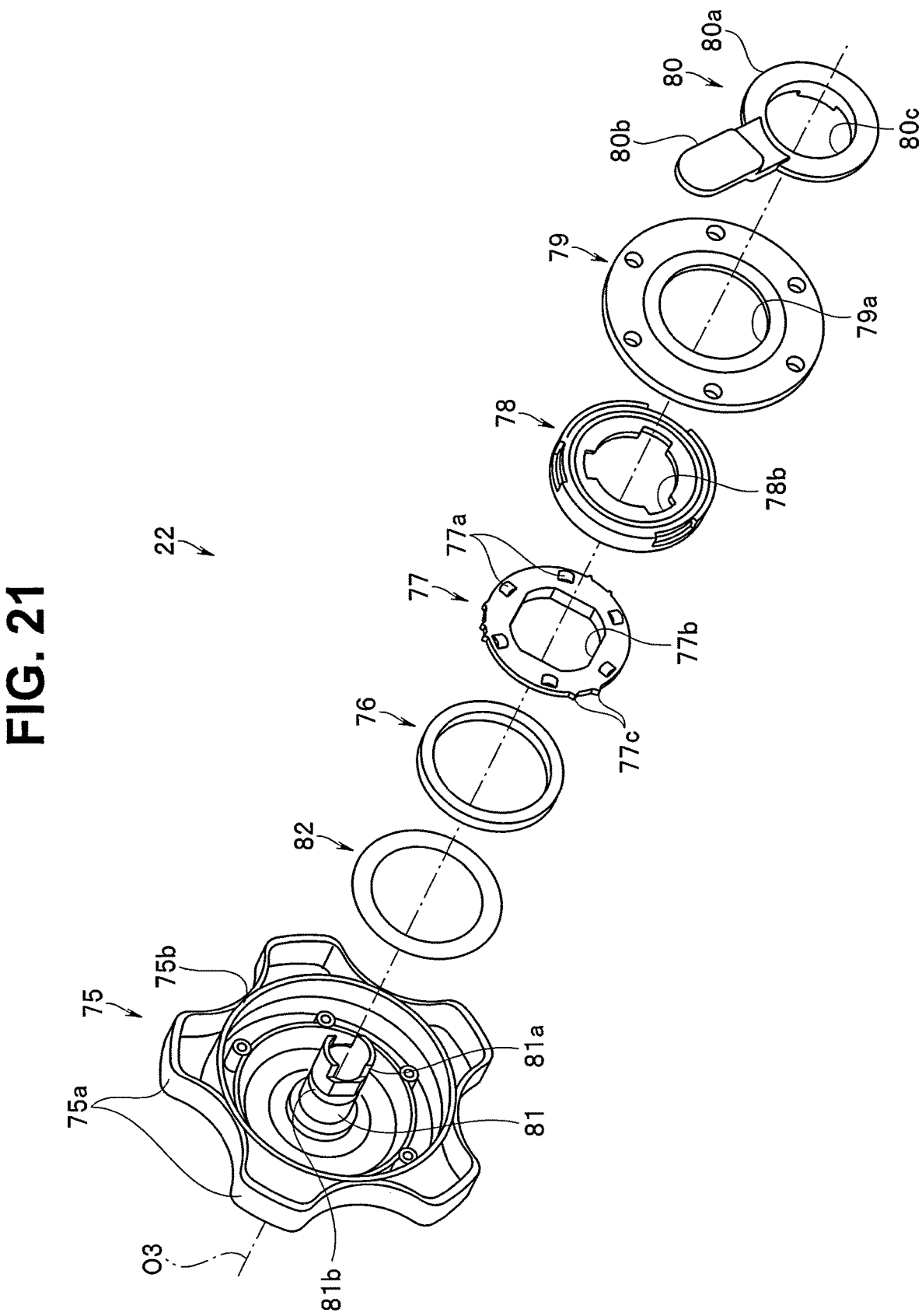
FIG. 21 is an exploded perspective view according to the first embodiment, and shows an up-down bending operation knob from one end side.
Figure 22:
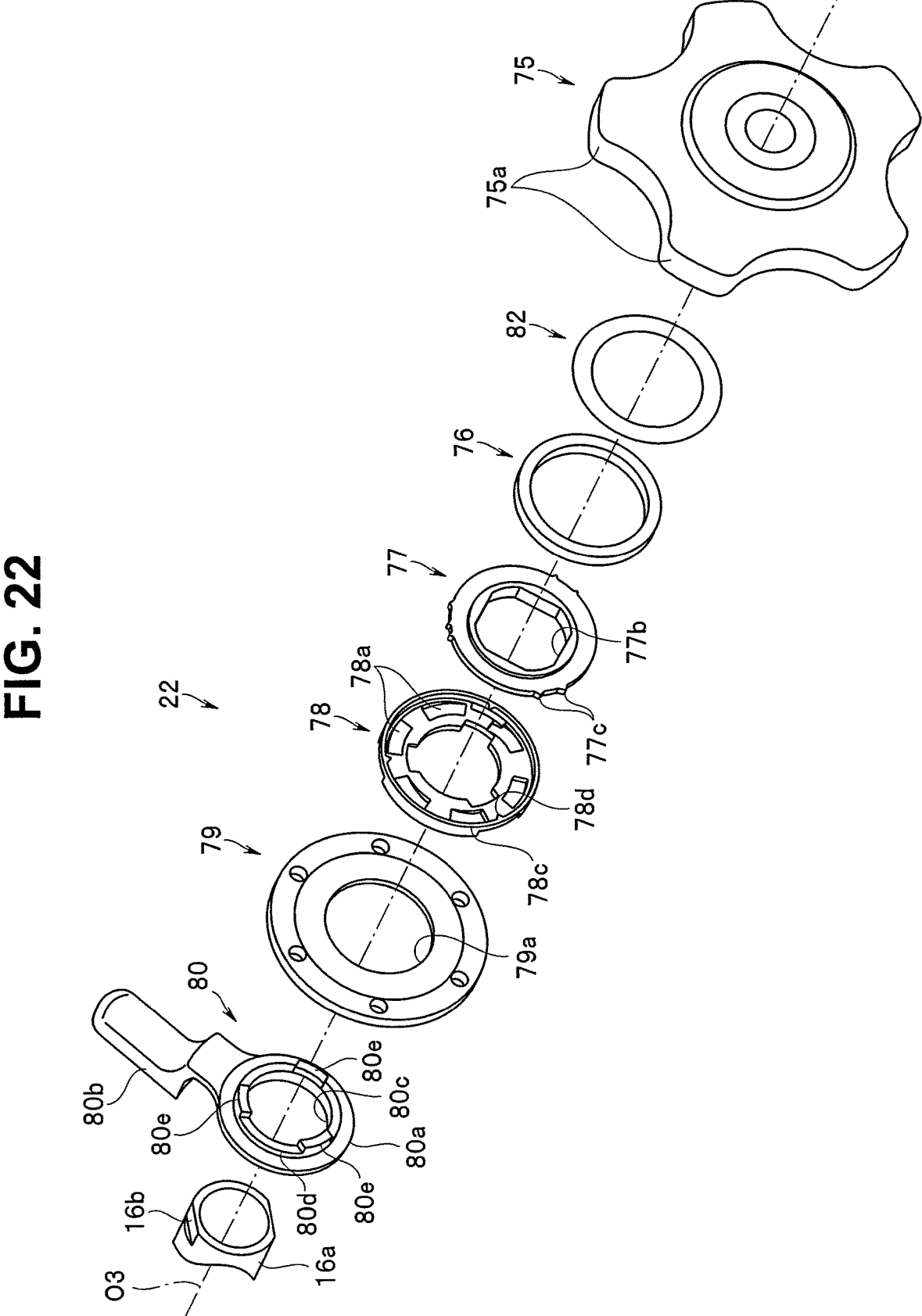
FIG. 22 is an exploded perspective view according to the first embodiment, and shows the up-down bending operation knob from the other end side.
Figure 23:
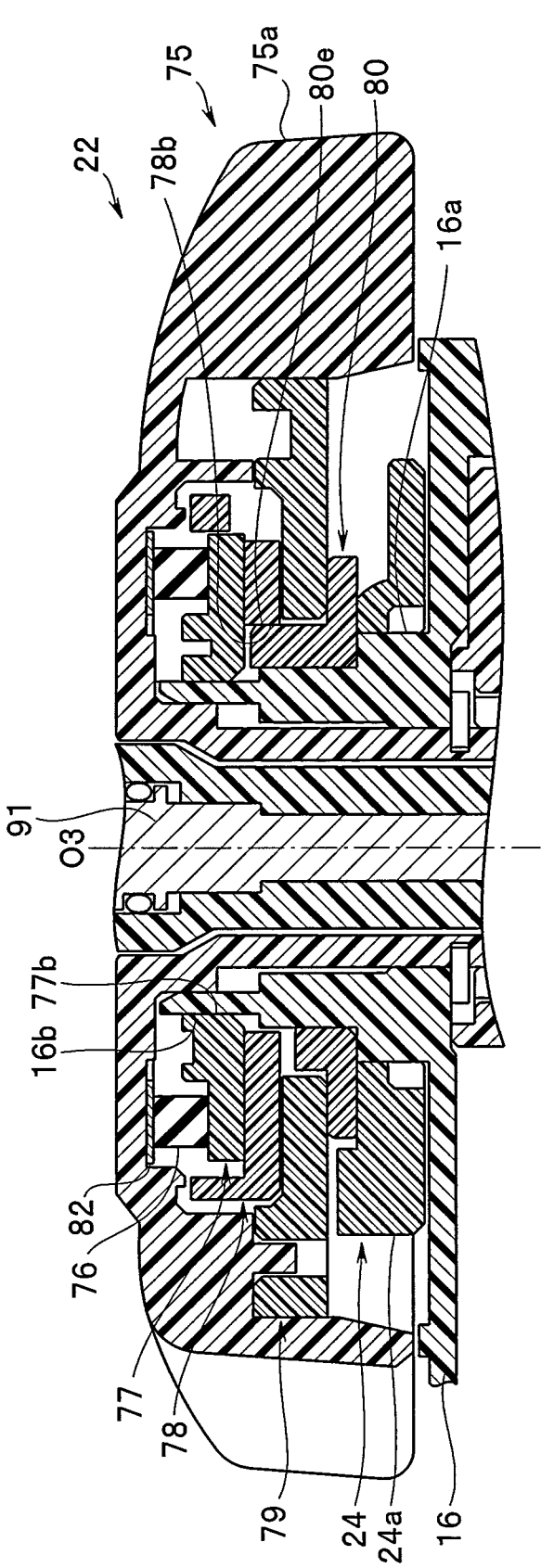
FIG. 23 is a cross-sectional view according to the first embodiment, and shows main parts of the up-down bending operation knob when the brake is released.
Figure 24:
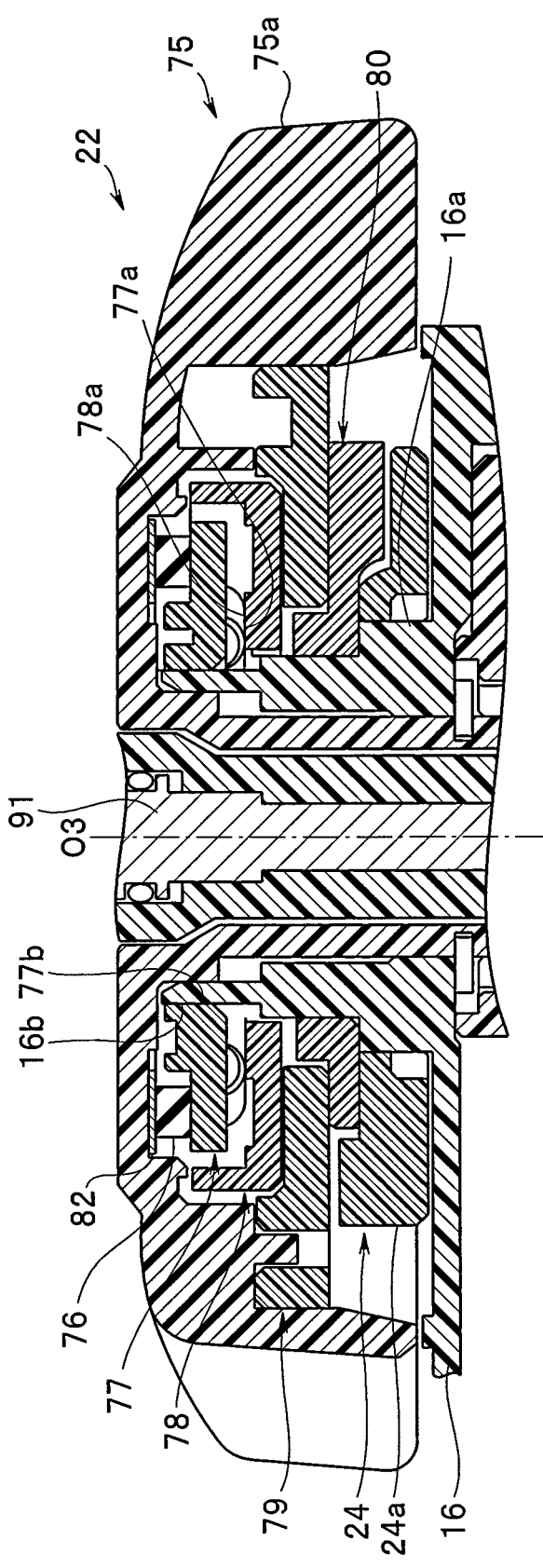
FIG. 24 is a cross-sectional view according to the first embodiment, and shows the main parts of the up-down bending operation knob when the brake is operated.

As shown in FIGS. 8, 21, and 22, the up-down bending operation knob 22 is a brake-integrated bending operation knob, for example. In other words, a brake mechanism configured to keep the up-down bending operation knob 22 at a turned position is integrally embedded in the up-down bending operation knob 22 of the present embodiment.

The up-down bending operation knob 22 includes an operation knob main body 75, friction rubber 76, a push plate 77, a cam plate 78, a lid 79, a brake operation lever 80, and a friction sheet 82.

The operation knob main body 75 is formed by a molded resin component, for example. The operation knob main body 75 includes a plurality of finger-hooking portions 75a that protrude radially. Furthermore, a brake chamber 75b is formed in the operation knob main body 75, on an inner side of the finger-hooking portions 75a. The brake chamber 75b has a substantially cylindrical shape where one end side in the center axis O3 direction is open.

Furthermore, a hollow shaft 81 that protrudes on the one end side in the center axis O3 direction is integrally formed at a center part of the operation knob main body 75 (a center part of the brake chamber 75b).

A key 81a that is capable of being fitted in the keyhole 51b in the up-down bending pulley 51 is provided at one end portion of the hollow shaft 81. The key 81a is shaped by cutting out a part of an outer peripheral portion on one end side of the hollow shaft 81, for example.

A fragile portion 81b is formed at a middle part of the hollow shaft 81. For example, the fragile portion 81b is formed by providing a groove on an outer periphery of the hollow shaft 81. Due to the fragile portion 81b, torsional strength of the hollow shaft 81 is set to be smaller than tensile strength of each up-down bending operation wire 37.

The friction rubber 76 is formed into an annular shape, for example. The friction rubber 76 is housed inside the brake chamber 75b across the friction sheet 82 that is annular.

The push plate 77 is formed by a molded resin component, for example. The push plate 77 is substantially disk-shaped. An outer diameter of the push plate 77 is set to be substantially the same as an outer diameter of the friction rubber 76.

A plurality of cam followers 77a formed as arc-shaped protrusions are formed on one end surface of the push plate 77, for example. The cam followers 77a are arranged on the one end surface of the push plate 77, annularly around the center axis O3.

Furthermore, a keyhole 77b that penetrates in the center axis O3 direction of the push plate 77 is provided at a center part of the push plate 77.

Furthermore, a plurality of small outward protrusions 77c that protrude in an outer diameter direction are provided at an outer peripheral portion of the push plate 77.

The push plate 77 structured in the above manner is housed inside the brake chamber 75b in a state where the other end surface is in contact with the friction rubber 76.

The cam plate 78 is formed by a molded resin component, for example. The cam plate 78 is substantially disk-shaped. An outer diameter of the cam plate 78 is set to be greater than the outer diameter of the push plate 77.

A plurality of cams 78a are formed on the other end surface of the cam plate 78 in the center axis O3 direction. Each cam 78a is formed as a sloping protrusion where an amount of protrusion toward the other end side gradually changes in a circumferential direction. The cams 78a are annularly arranged on the other end surface of the cam plate 78 in a manner facing the respective cam followers 77*a*.

Furthermore, a keyhole 78*b* that penetrates in the center axis O3 direction of the cam plate 78 is provided at a center part of the cam plate 78.

Furthermore, a flange 78*c* that is annular and that protrudes on the other end side is formed on an outer edge portion of the cam plate 78. The flange 78*c* has an inner diameter that is greater than the outer diameter of the push plate 77.

A plurality of small inward protrusions 78*d* that protrude in an inner diameter direction are provided on an inner peripheral portion of the flange 78*c*. The inward protrusions 78*d* are capable of engaging with the respective outward protrusions 77*c* provided on the push plate 77.

The cam plate 78 structured in the above manner is housed inside the brake chamber 75*b* in a state where the push plate 77 is housed inside the flange 78*c*.

The lid 79 is formed by a molded resin component, for example. The lid 79 is substantially disk-shaped. An outer diameter of the lid 79 is set to be substantially the same as an inner diameter of the brake chamber 75*b*.

A through hole 79*a* that penetrates in the center axis O3 direction of the lid 79 is provided in the lid 79.

The lid 79 is fixed to the operation knob main body 75 by screwing or the like in a state of being housed inside the brake chamber 75*b*.

The brake operation lever 80 is formed by a molded resin component, for example. The brake operation lever 80 includes a rotating plate 80*a* that is substantially disk-shaped, and a lever 80*b* that protrudes in an outer diameter direction of the rotating plate 80*a*, for example.

A through hole 80*c* that penetrates in the center axis O3 direction of the rotating plate 80*a* is provided at a center part of the rotating plate 80*a*.

Furthermore, a flange 80*d* that is annular and that protrudes on the other end side is formed on an inner edge portion of the rotating plate 80*a*. An outer diameter of the flange 80*d* is set to be substantially the same as an inner diameter of the through hole 79*a* in the lid 79. The flange 80*d* is slidably fitted in the through hole 79*a* in the lid 79.

Furthermore, a key 80*e* that can be fitted in the keyhole 78*b* in the cam plate 78 protrudes from a part of the flange 80*d*. When the key 80*e* is fitted in the keyhole 78*b* in the cam plate 78, the brake operation lever 80 can be integrally turned with the cam plate 78.

In relation to the up-down bending operation knob 22, the hollow shaft 81 protrudes on the one end side than the brake operation lever 80, through each center part of the friction sheet 82, the friction rubber 76, the push plate 77, the cam plate 78, the lid 79, and the brake operation lever 80.

As shown in FIGS. 3, 8, 23, and 24, the up-down bending operation knob 22 structured in the above manner is attached to the first housing member 16 via a shaft cylinder 16*a* that protrudes from the side portion of the first housing member 16.

More specifically, the hollow shaft 81 of the up-down bending operation knob 22 is turnably inserted inside the shaft cylinder 16*a*. The up-down bending operation knob 22 is thereby turnably supported by the first housing member 16.

In the present case, a key 16*b* provided at one end portion of the shaft cylinder 16*a* is fitted in the keyhole 51*b* in the up-down bending pulley 51. The up-down bending pulley 51 is thus able to turn according to a turning operation on the up-down bending operation knob 22. Moreover, the up-down bending pulley 51 pulls or loosens the pair of up-down bending operation wires 37 according to a turned state. The up-down bending operation knob 22 is thereby able to bend the bending portion 11 in the up-down direction via the pulley unit 36.

Note that, in a case where an excessive operation force is inputted to the up-down bending pulley 51 at a time of such a bending operation, the fragile portion 81*b* of the hollow shaft 81 gets broken before each up-down bending operation wire 37 gets ruptured. Accordingly, rupture of each up-down bending operation wire 37 is prevented.

The key 16*b* is provided at a protruding end portion of the shaft cylinder 16*a* (the other end portion of the shaft cylinder 16 in the center axis O3 direction) that protrudes from the first housing member 16. For example, the key 16*b* is shaped by cutting out a part of an outer peripheral portion on the other end side of the shaft cylinder 16*a*. The key 16*b* is fitted in the keyhole 77*b* in the push plate 77 by penetrating through the brake operation lever 80, the lid 79, and the cam plate 78. The push plate 77 is thereby supported by the shaft cylinder 16*a* (the first housing member 16) in a non-turnable manner.

When the cam plate 78 is turned by an operation on the brake operation lever 80, the push plate 77 rotates relative to the cam plate 78. Due to the relative rotation, contact positions of the cam followers 77*a* on the cams 78*a* are changed. Due to the change in the contact positions, the push plate 77 is displaced toward the operation knob main body 75 side (see a change from FIG. 23 to FIG. 24). The friction rubber 76 is thus pressed against the friction sheet 82 and the operation knob main body 75 while being elastically deformed by a pressing force from the push plate 77. Moreover, due to the pressing force from the push plate 77, a great frictional force is generated between the operation knob main body 75 and the friction sheet 82, and between the cam plate 78 and the lid 79. Here, the push plate 77 is not turnable relative to the shaft cylinder 16*a*. Accordingly, turning of the operation knob main body 75 is restricted. Because turning of the operation knob main body 75 is restricted, the turned position of the up-down bending operation knob 22 is maintained (the brake is operated). Note that when the up-down bending operation knob 22 is forcibly turned after the turned position of the up-down bending operation knob 22 is temporarily maintained, the cam plate 78 may be turned and the pressing force of the push plate 77 may be reduced, and the frictional force is possibly reduced. The inward protrusions 78*d* of the flange 78*c* engage with the respective outward protrusions 77*c* provided on the push plate 77 to prevent turning of the cam plate 78. Accordingly, even when the up-down bending operation knob 22, the turned position of which is maintained, is forcibly turned, turning of the cam plate 78 is restricted. As a result, the pressing force from the push plate 77 is not reduced, and the frictional force is not reduced.

As shown in FIGS. 8, and 14 to 20, the left-right bending operation knob 23 is a brake-integrated bending operation knob, for example. In other words, a brake mechanism configured to keep the left-right bending operation knob 23 at a turned position is integrally embedded in the left-right bending operation knob 23 of the present embodiment.

The left-right bending operation knob 23 includes an operation knob main body 85, a cam plate 86, a push plate 87, friction rubber 88, a lid 89, a brake operation knob 90, a fixing shaft 91, and a friction sheet 93.

The operation knob main body 85 is formed by a molded resin component, for example. The operation knob main body 85 includes a plurality of finger-hooking portions 85*a* that protrude radially. Furthermore, a brake chamber 85*b* is formed on the operation knob main body 85, on an inner side of the finger-hooking portions 85*a*. One end side of the brake chamber 85*b* in the center axis O3 direction is open.

Furthermore, a through hole 85*c* that penetrates in the center axis O3 direction of the operation knob main body 85 is provided at a center part of the operation knob main body 85.

The cam plate 86 is formed by a molded resin component, for example. The cam plate 86 is substantially disk-shaped.

A plurality of cams 86*a* are formed on one end surface of the cam plate 86 in the center axis O3 direction. Each cam 86*a* is formed as a sloping protrusion where an amount of protrusion toward the one end side gradually changes in a circumferential direction. The cams 86*a* are arranged on the one end surface of the cam plate 86, annularly around the center axis O3.

Furthermore, a through hole 86*b* that penetrates in the center axis O3 direction of the cam plate 86 is provided at a center part of the cam plate 86. Furthermore, a keyhole 86*c* that penetrates in the center axis O3 direction of the cam plate 86 is provided around the through hole 86*b* in the cam plate 86.

Furthermore, a flange 86*d* that is annular and that protrudes on the one end side is formed on an outer edge portion of the cam plate 86. A plurality of small inward protrusions 86*e* that protrude in an inner diameter direction are provided on an inner peripheral portion of the flange 86*d*.

The cam plate 86 structured in the above manner is housed inside the brake chamber 85*b*.

The push plate 87 is formed by a molded resin component, for example. The push plate 87 is substantially disk-shaped. An outer diameter of the push plate 87 is set to be smaller than an inner diameter of the flange 86*d* of the cam plate 86.

A plurality of cam followers 87*a* formed as arc-shaped protrusions are formed on the other end surface of the push plate 87, for example. The cam followers 87*a* are annularly arranged on the other end surface of the push plate 87 to face the respective cams 86*a*.

Furthermore, a keyhole 87*b* that penetrates in the center axis O3 direction of the push plate 87 is provided at a center part of the push plate 87.

Furthermore, a plurality of small outward protrusions 87*c* that protrude in an outer diameter direction are provided at an outer peripheral portion of the push plate 87. The outward protrusions 87*c* are capable of engaging with the respective inward protrusions 86*e* provided on the cam plate 86.

The push plate 87 structured in the above manner is housed inside the flange 86*d* of the cam plate 86.

The friction rubber 88 is formed into an annular shape, for example. The friction rubber 88 is housed inside the brake chamber 85*b* in a state of being in contact with the push plate 87.

The lid 89 is formed by a molded resin component, for example. The lid 89 has a substantially flat plate shape that is approximately similar to a plan-view shape of the operation knob main body 85.

A hollow shaft 92 that protrudes on one end side in the center axis O3 direction is integrally formed with the lid 89.

A key 92*a* that can be fitted in the keyhole 52*b* in the left-right bending pulley 52 is provided at one end portion of the hollow shaft 92. The key 92*a* is shaped by cutting out a part of an outer peripheral portion on one end side of the hollow shaft 92, for example.

The key 92*a* is set as a fragile portion that is plastically deformed when an external force is applied with a predetermined magnitude or more. Torsional strength of the key 92*a* is set to be smaller than tensile strength of each left-right bending operation wire 38.

The lid 89 is fixed to the operation knob main body 85 by screwing or the like while abutting against one end side of the operation knob main body 85. In the present case, the friction rubber 88 abuts against the lid 89 across the annular friction sheet 93.

The brake operation knob 90 is formed by a molded resin component, for example. The brake operation knob 90 includes a rotating member 90*a* that has a gradually sloping, substantially frusto-conical shape, and a knob 90*b* that protrudes on the other end side of the rotating member 90*a*.

A through hole 90*c* that penetrates the rotating member 90*a* and the knob 90*b* in the center axis O3 direction is provided at a center part of the brake operation knob 90.

Furthermore, a key 90*d* that can be fitted in the keyhole 86*c* in the cam plate 86 protrudes from one end surface of the rotating member 90*a*.

The rotating member 90*a* of the brake operation knob 90 turnably abuts against the other end side of the operation knob main body 85. In the present state, the key 90*d* of the brake operation knob 90 is fitted in the keyhole 86*c* in the cam plate 86 through the through hole 85*c* in the operation knob main body 85. Accordingly, the brake operation knob 90 can turn together with the cam plate 86.

The fixing shaft 91 is formed by a cut metal component, for example. A key 91*a* that can fit in the keyhole 87*b* in the push plate 87 is provided at a middle part of the fixing shaft 91.

The fixing shaft 91 is inserted inside the hollow shaft 92 through each center part of the brake operation knob 90, the operation knob main body 85, the cam plate 86, the push plate 87, the friction rubber 88, and the friction sheet 93. In the present state, the key 91*a* of the fixing shaft 91 is fitted in the keyhole 87*b* in the push plate 87.

As shown in FIG. 8, the left-right bending operation knob 23 structured in the above manner is attached to the first housing member 16 by having the hollow shaft 92 of the left-right bending operation knob 23 inserted in the hollow shaft 81 of the up-down bending operation knob 22.

In the present case, the key 92*a* provided at one end portion of the hollow shaft 92 is fitted in the keyhole 52*b* in the left-right bending pulley 52. The left-right bending pulley 52 can thereby turn according to a turning operation on the left-right bending operation knob 23. The left-right bending pulley 52 pulls or loosens the pair of left-right bending operation wires 38 according to a turned state. The left-right bending operation knob 23 can thereby bend the bending portion 11 in the left-right direction via the pulley unit 36.

Note that, in a case where an excessive operation force is inputted to the left-right bending operation knob 23 at a time of such a bending operation, the key 92*a* of the hollow shaft 92 gets broken before each left-right bending operation wire 38 gets ruptured. Accordingly, rupture of each left-right bending operation wire 38 is prevented.

Here, as shown in FIG. 8, one end portion of the fixing shaft 91 inserted in the hollow shaft 92 is coupled to the shaft hole 62*a* in the second case member 62 in a non-turnable manner. Accordingly, the push plate 87 is supported by the shaft cylinder 16*a* (the first housing member 16) in a non-turnable manner.

When the cam plate 86 is turned by an operation on the brake operation knob 23, the push plate 87 rotates relative to the cam plate 86. Due to the relative rotation, contact positions of the cam followers 87*a* on the cams 86*a* are changed. Due to the change in the contact positions, the push plate 87 is displaced toward the lid 89 side (see a change from FIG. 19 to FIG. 20). The friction rubber 88 is thus pressed against the friction sheet 93 and the lid 89 while being elastically deformed by a pressing force from the push plate 87. Moreover, due to the pressing force from the push plate 87, a great frictional force is generated between the lid 89 and the friction sheet 93, and between the cam plate 86 and the operation knob main body 85. Here, the push plate 87 is not turnable relative to the fixing shaft 91. Furthermore, the lid 89 is fixed to the operation knob main body 85 in a non-turnable manner. Accordingly, turning of the operation knob main body 85 is restricted. Because turning of the operation knob main body 85 is restricted, the turned position of the left-right bending operation knob 23 is maintained. Note that when the left-right bending operation knob 23 is forcibly turned after the turned position of the left-right bending operation knob 23 is temporarily maintained, the cam plate 86 may be turned and the pressing force of the push plate 87 may be reduced, and the frictional force is possibly reduced. The inward protrusions 86e of the flange 86d engage with the respective outward protrusions 87c provided on the push plate 87 to prevent turning of the cam plate 86. Accordingly, even when the left-right bending operation knob 23, the turned position of which is maintained, is forcibly turned, turning of the cam plate 86 is restricted. As a result, the pressing force from the push plate 87 is not reduced, and the frictional force is not reduced.

Next, a structure of the raising base operation mechanism 40 will be described in detail.

Figure 25:
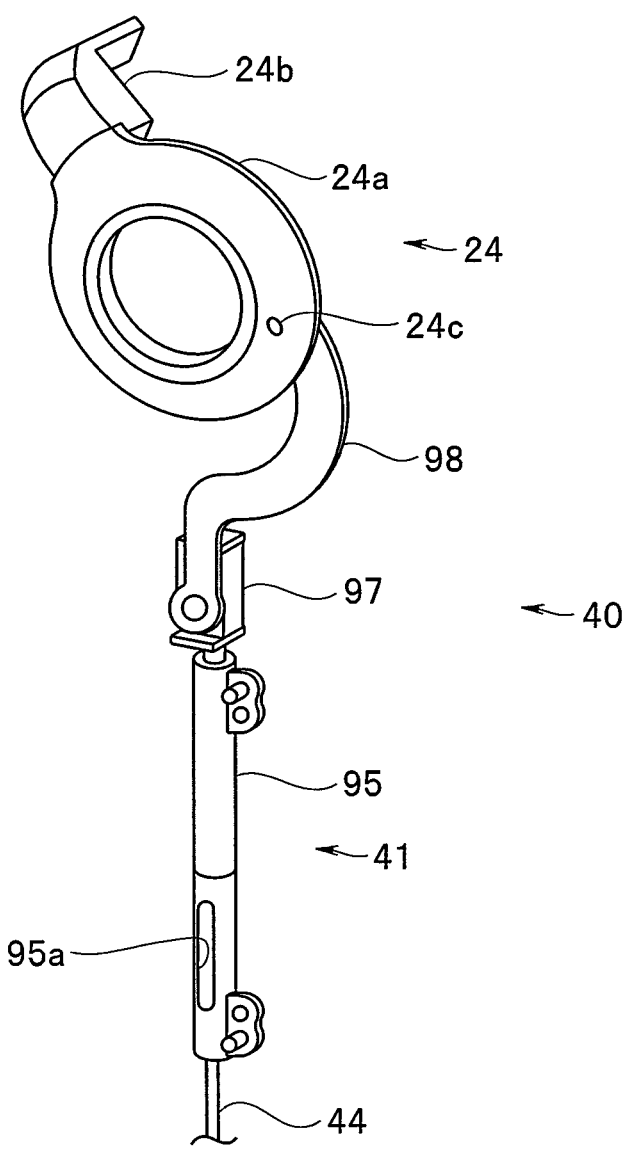
FIG. 25 is a perspective view according to the first embodiment, and shows a raising base (forceps elevator) operation mechanism.
Figure 26:
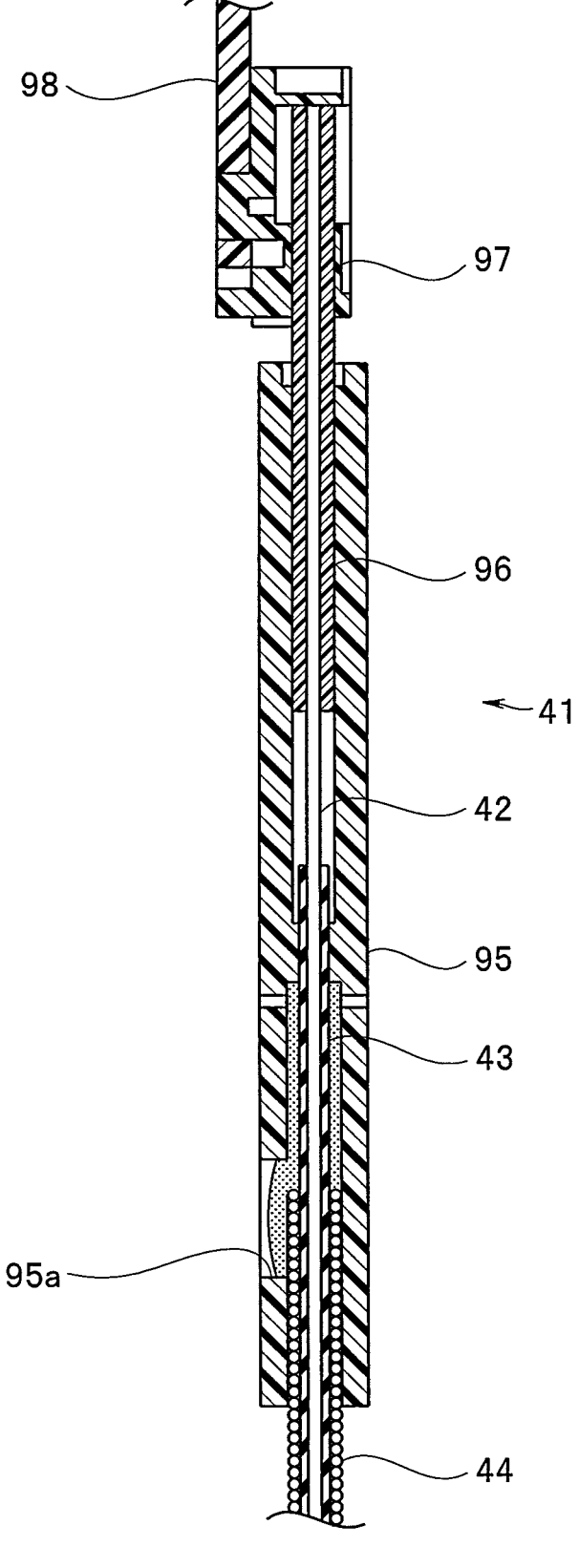
FIG. 26 is a cross-sectional view according to the first embodiment, and shows main parts of a cylinder unit.
Figure 27:
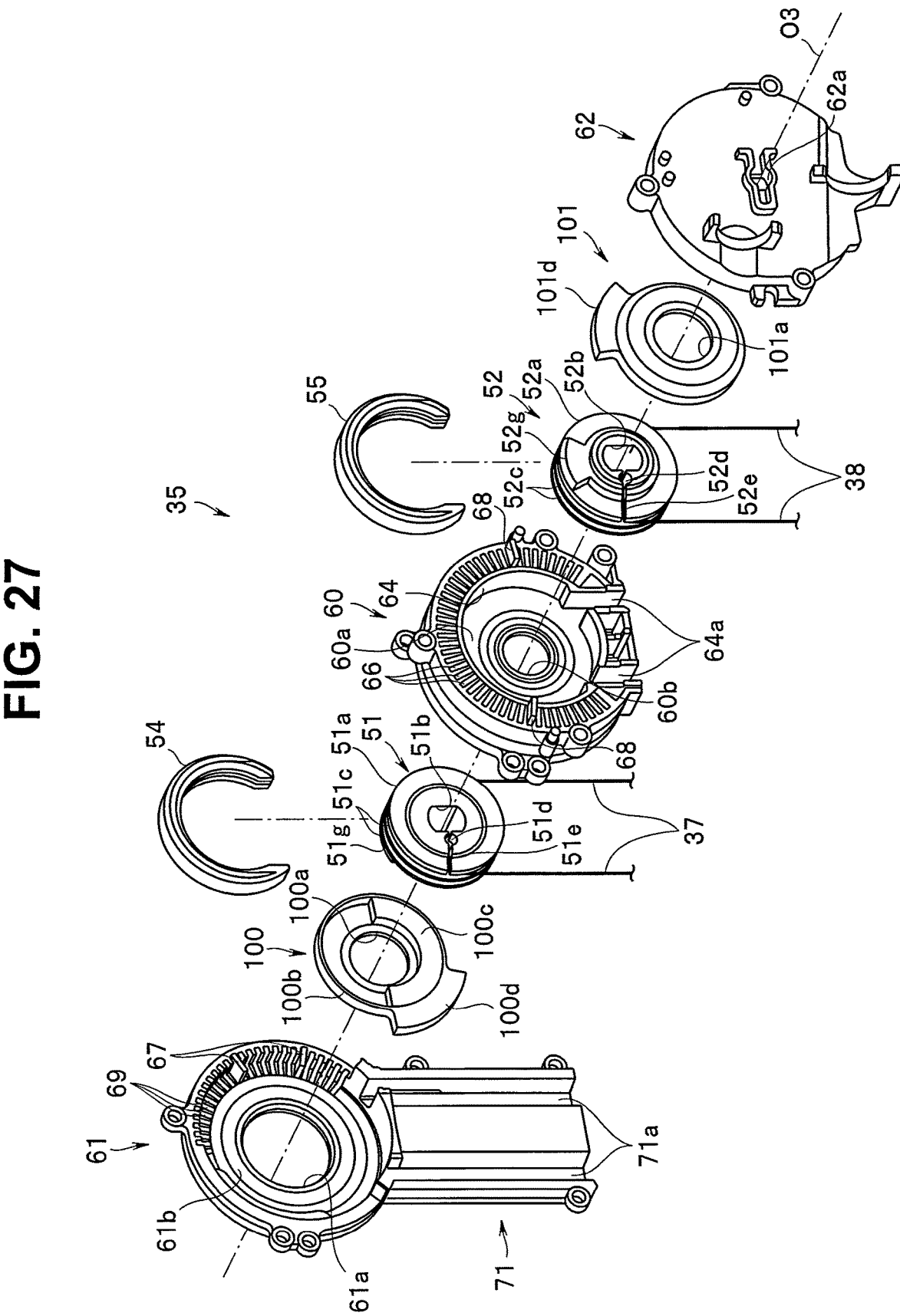
FIG. 27 is an exploded perspective view according to a second embodiment, and shows a bending operation mechanism main body from one end side.
Figure 28:
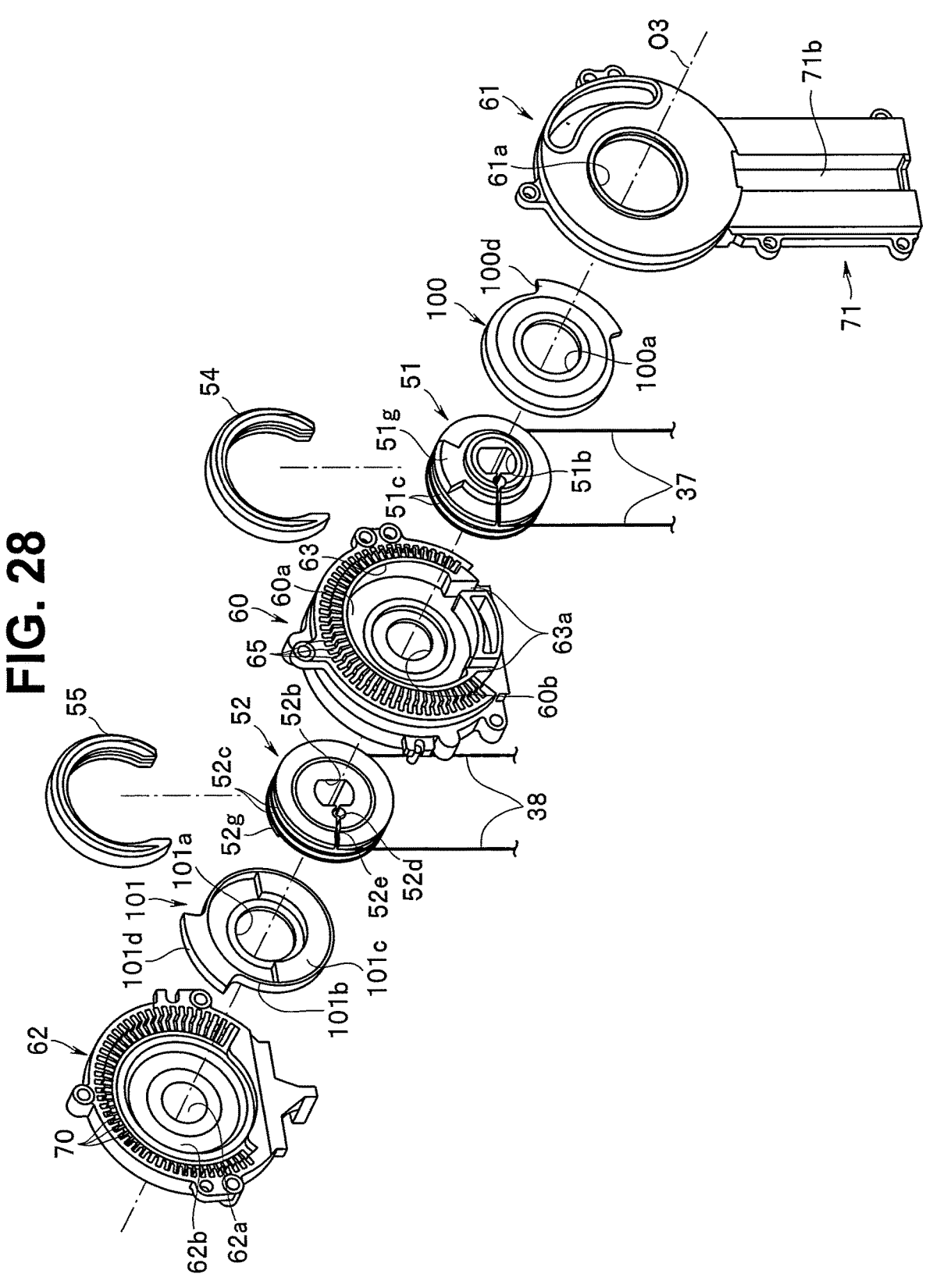
FIG. 28 is an exploded perspective view according to the second embodiment, and shows the bending operation mechanism main body from the other end side.
Figure 29:
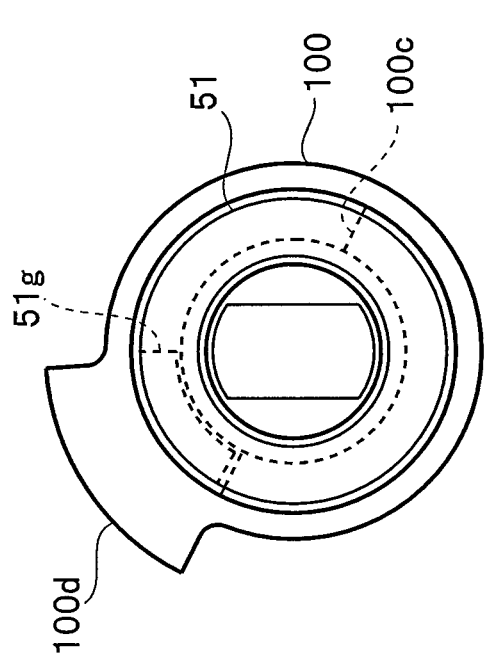
FIG. 29 is a plan view according to the second embodiment, and schematically shows a state where an up-down bending pulley is turned to a first turning end position of an auxiliary plate.
Figure 30:
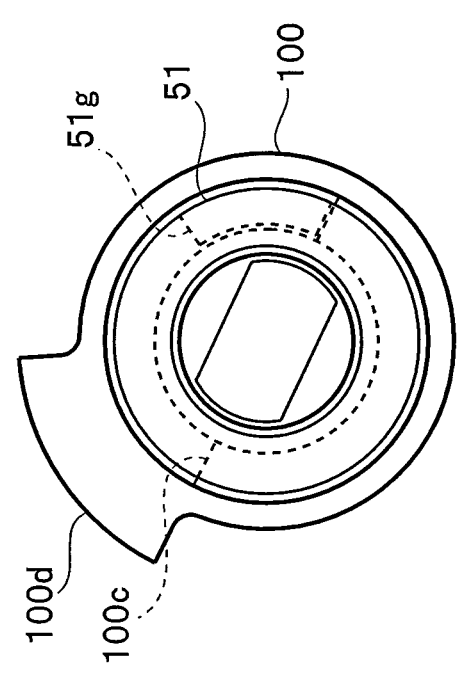
FIG. 30 is a plan view according to the second embodiment, and schematically shows a state where the up-down bending pulley is turned to a second turning end position of the auxiliary plate.

As shown in FIGS. 25 and 26, the cylinder unit 41 of the raising base operation mechanism 40 includes a cylinder 95 that allows insertion of a proximal end side of the raising base operation wire 42. A rod 96 is inserted in a proximal end side of the cylinder 95 in a manner capable of freely moving forward and backward.

A proximal end portion of the raising base operation wire 42 is connected to the rod 96. More specifically, the proximal end side of the raising base operation wire 42 is inserted into the cylinder 95 from a distal end side of the cylinder 95. Inside the cylinder 95, the proximal end portion of the raising base operation wire 42 is exposed from a sheath 43. Moreover, the proximal end portion of the raising base operation wire 42 that is exposed from the sheath 43 is connected to the rod 96. Outside the cylinder 95, a head member 97 is connected to a proximal end side of the rod 96. The head member 97 is slidable in a recessed portion 71b (see FIG. 10) provided on the bracket 71. Accordingly, the head member 97 is guided by the recessed portion 71b, and is capable of moving in the longitudinal axis O2 direction of the housing 15.

Furthermore, a communication hole 95a that allows inside and outside of the cylinder 95 to communicate is provided in a side portion on a distal end side of the cylinder 95. Near the communication hole 95a, a proximal end side of a guide coil 44 that covers the sheath 43 of the raising base operation wire 42 is inserted inside the cylinder 95. The coil 44 and the sheath 43 are fixed by adhesion to an inner peripheral surface of the cylinder 95 by injection of an adhesive from the communication hole 95a into the cylinder 95.

The raising base operation lever 24 includes a rotating cam 24a that is annular and plate-shaped, and a lever 24b that protrudes in an outer diameter direction of the rotating cam 24a. The rotating cam 24a and the lever 24b are integrally formed by molding resin, for example.

As shown in FIG. 8, the rotating cam 24a is disposed between the up-down bending operation knob 22 and the first housing member 16. The shaft cylinder 16a is inserted in the rotating cam 24a. The raising base operation lever 24 is thus turnably supported by the first housing member 16.

A cam pin 24c that protrudes on the first housing member 16 side is provided on the rotating cam 24a. The cam pin 24c is inserted in an arc-shaped keyhole 16c provided in the first housing member 16. Turning of the raising base operation lever 24 is restricted within an angle range where the lever 24b abuts against two protrusions formed on the first housing member 16, for example. Note that turning of the raising base operation lever 24 can also be restricted within an angle range where the cam pin 24c moves from one end side to the other end side of the keyhole 16c.

Furthermore, inside the first housing member 16, the cam pin 24c is connected to the head member 97 of the cylinder unit 41 via a relay member 98. The rod 96 thereby moves forward and backward inside the cylinder 95 according to a turning operation on the raising base operation lever 24. The raising base operation wire 42 is pulled or loosened by the forward/backward movement of the rod 96. The raising base 10c provided on the distal end portion 10 is thereby allowed to be displaced between a raised position and a lowered position.

According to such an embodiment, the endoscope bending operation mechanism 35 includes the up-down bending operation knob 22 (and the left-right bending operation knob 23), the up-down bending pulley 51 (and the left-right bending pulley 52) configured to turn by an operation force from the up-down bending operation knob 22 (and the left-right bending operation knob 23), the up-down bending operation wire 37 (and the left-right bending operation wire 38), a proximal end side of which is wound around the up-down bending pulley 51 (and the left-right bending pulley 52) and a distal end side of which is coupled to the bending portion 11 of the insertion section 5, the pulley case 53 that holds the up-down bending pulley 51 (and the left-right bending pulley 52), the stopper member 67 (and the stopper member 68) that is removable relative to the pulley case 53, and the plurality of mounting portions 65 (and the mounting portions 66, 69, 70) for mounting the stopper member 67 (and the stopper member 68) on the pulley case 53.

Accordingly, the endoscope bending operation mechanism 35 that has a simple structure can be manufactured at a low cost by reducing the number of dedicated parts.

In other words, the endoscope bending operation mechanism 35 is capable of adjusting a turning angle range of the up-down bending pulley 51 (and the left-right bending pulley 52) according to an attached position of the stopper member 67 (and the stopper member 68) on the plurality of mounting portions 65 (and the plurality of mounting portions 66). Accordingly, components of the endoscope bending operation mechanism 35 can be made common among various types of endoscopes 1, and the endoscope bending operation mechanism 35 that has a simple structure can be manufactured at a low cost.

Furthermore, with the endoscope bending operation mechanism 35, a bending angle and the like of the bending portion 11 can be finely adjusted simply by adjusting/changing the attached position of the stopper member 67 (and the stopper member 68) on the plurality of mounting portions 65 (and the plurality of mounting portions 66). Accordingly, for example, even in a case where there is an error in a length or the like of the up-down bending operation wire 37 (and the left-right bending operation wire 38) due to a manufacturing error or the like, the bending angle and the like can be easily adjusted without adding an adjustment mechanism to each wire.

Furthermore, the pulley unit 36 is fixed to the housing 15 (the first housing member 16) by the pulley case 53. Accordingly, the pulley unit 36 can be fixed to the housing 15 by a simple structure without providing, inside the housing 15, a bracket or the like that is formed from a base plate or the like. In the present case, attachment strength of the pulley unit 36 to the housing 15 can be set smaller for a single-use endoscope than for a reusable endoscope. Accordingly, when the bracket 71 is formed by a molded resin component, the first case member 61 and the bracket 71 can be easily and integrally formed.

Furthermore, in the present embodiment, the up-down bending operation knob 22 and the left-right bending operation knob 23 each include a fragile portion that gets broken when an excessive operation force is inputted. Such a fragile portion is set weaker than the tensile strength of the corresponding bending operation wire. Accordingly, when an excessive operation force is inputted to each bending operation knob, the fragile portion gets broken before each bending operation wire gets ruptured. Each bending operation wire can thereby be appropriately prevented from getting ruptured inside the insertion section 5.

Furthermore, the bending operation member can be like one or more wheels, levers and buttons that are movable to provide the operation force to the pulley to move the pulley.

Next, a second embodiment of the present disclosure will be described with reference to FIGS. 27 to 33. Note that the present embodiment is different from the first embodiment described above mainly with respect to the structure of the pulley unit 36. Other components the same as the components of the first embodiment will be denoted by same reference signs, and redundant description will be omitted.

The up-down bending pulley 51 of the present embodiment includes an auxiliary protruding portion 51g instead of the protruding portion 51f described above. The auxiliary protruding portion 51g protrudes in a thickness direction of the up-down bending pulley main body 51a. More specifically, the auxiliary protruding portion 51g has a partial arc shape having an outer diameter that is substantially the same as an outer diameter of the up-down bending pulley main body 51a. For example, the auxiliary protruding portion 51g protrudes on the other end side of the up-down bending pulley main body 51a in the center axis O3 direction.

Furthermore, an auxiliary plate 100 is interposed between the up-down bending pulley 51 and the first case member 61. The auxiliary plate 100 is substantially disk-shaped. An outer diameter of the auxiliary plate 100 is set to be greater than an outer diameter of the up-down bending pulley 51.

A through hole 100a that penetrates in the center axis O3 direction of the auxiliary plate 100 is provided at a center part of the auxiliary plate 100.

Furthermore, an annular flange 100b that protrudes on the one end side along the center axis O3 is formed at an outer edge portion of the auxiliary plate 100. An inner diameter of the flange 100b is set to be substantially the same as the outer diameter of the auxiliary protruding portion 51g. The auxiliary protruding portion 51g of the up-down bending pulley 51 is inserted in the flange 100b. The up-down bending pulley 51 is thereby connected to the auxiliary plate 100 in a turnable manner.

Furthermore, an auxiliary stopper 100c having a partial arc shape is formed inside the flange 100b. The auxiliary stopper 100c is capable of abutting against the auxiliary protruding portion 51g. A relative turning angle range between the auxiliary plate 100 and the up-down bending pulley 51 is thereby defined by the auxiliary stopper 100c and the auxiliary protruding portion 51g (see FIGS. 29 and 30).

Furthermore, a protruding portion 100d as an abutting portion is provided on the auxiliary plate 100. The protruding portion 100d has a partial arc shape, and protrudes in an outer diameter direction of the auxiliary plate 100, for example.

When the auxiliary plate 100 is interposed, together with the up-down bending pulley 51, between the case main body 60 and the first case member 61, the protruding portion 100d is disposed at a position that faces the other end surface of the case main body 60. In other words, the protruding portion 100d is disposed at a position where the protruding portion 100d is capable of abutting against each stopper member 67. The auxiliary plate 100 is thereby capable of turning inside the pulley case 53 in an angle range defined by each stopper member 67.

Figure 31:
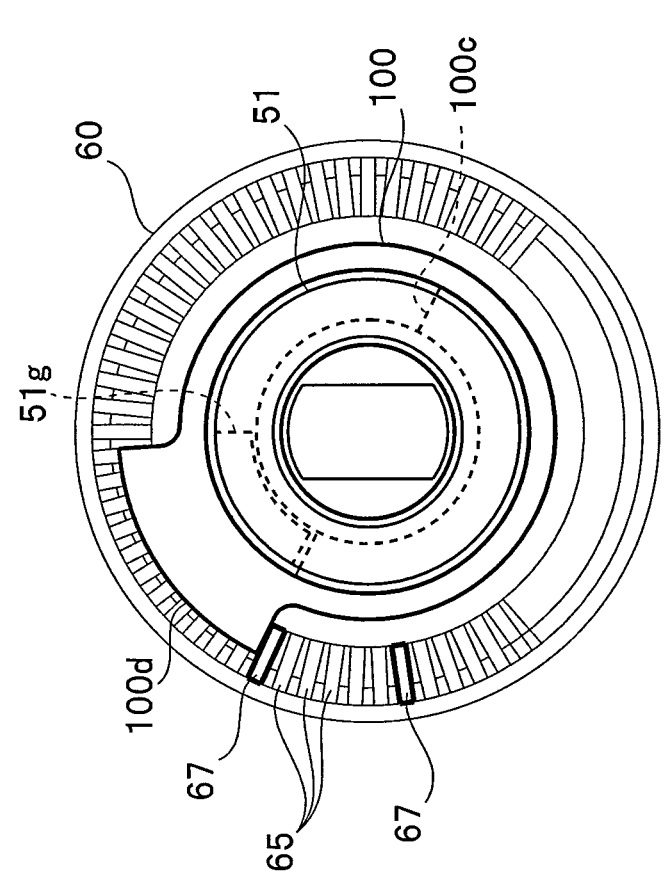
FIG. 31 is a plan view according to the second embodiment, and schematically shows a state where the up-down bending pulley and the auxiliary plate are turned to the first turning end position.
Figure 32:
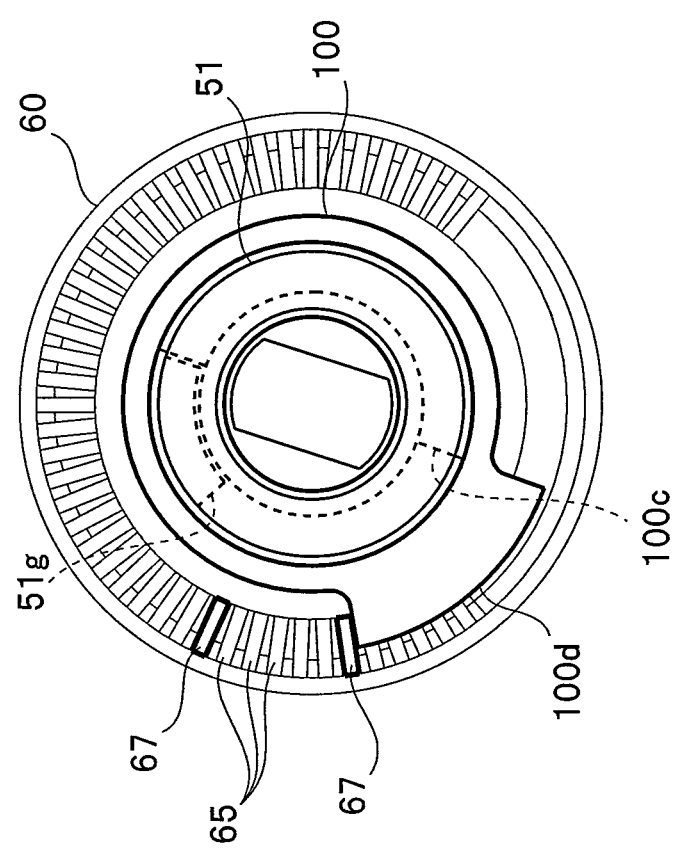
FIG. 32 is a plan view according to the second embodiment, and schematically shows a state where the up-down bending pulley and the auxiliary plate are turned to the second turning end position.

Accordingly, the up-down bending pulley 51 is allowed to turn in an angle range combining the angle range allowed for the up-down bending pulley 51 by the auxiliary plate 100 and the angle range allowed for the auxiliary plate 100 by the pulley case 53 (see FIGS. 31 and 32).

Furthermore, the left-right bending pulley 52 of the present embodiment includes an auxiliary protruding portion 52g instead of the protruding portion 52f described above. The auxiliary protruding portion 52g protrudes in a thickness direction of the left-right bending pulley main body 52a. More specifically, the auxiliary protruding portion 52g has a partial arc shape having an outer diameter that is substantially the same as an outer diameter of the left-right bending pulley main body 52a. For example, the auxiliary protruding portion 52g protrudes on the one end side of the left-right bending pulley main body 52a in the center axis O3 direction.

Furthermore, an auxiliary plate 101 is interposed between the left-right bending pulley 52 and the second case member 62. The auxiliary plate 101 is substantially disk-shaped. An outer diameter of the auxiliary plate 101 is set to be greater than an outer diameter of the left-right bending pulley 52.

A through hole 101a that penetrates in the center axis O3 direction of the auxiliary plate 101 is provided at a center part of the auxiliary plate 101.

Furthermore, an annular flange 101b that protrudes on the other end side along the center axis O3 is formed at an outer edge portion of the auxiliary plate 101. An inner diameter of the flange 101b is set to be substantially the same as the outer diameter of the auxiliary protruding portion 52g. The auxiliary protruding portion 52g of the left-right bending pulley 52 is inserted in the flange 101b. The left-right bending pulley 52 is thereby connected to the auxiliary plate 101 in a turnable manner.

Furthermore, an auxiliary stopper 101c having a partial arc shape is formed inside the flange 101b. The auxiliary stopper 101c is capable of abutting against the auxiliary protruding portion 52g. A relative turning angle range between the auxiliary plate 101 and the left-right bending pulley 52 is thereby defined by the auxiliary stopper 101c and the auxiliary protruding portion 52g.

Furthermore, a protruding portion 101d as an abutting portion is provided on the auxiliary plate 101. The protruding portion 101d has a partial arc shape, and protrudes in an outer diameter direction of the auxiliary plate 101, for example.

When the auxiliary plate 101 is interposed, together with the left-right bending pulley 52, between the case main body 60 and the second case member 62, the protruding portion 101*d* is disposed at a position that faces the one end surface of the case main body 60. In other words, the protruding portion 101*d* is disposed at a position where the protruding portion 101*d* is capable of abutting against each stopper member 68. The auxiliary plate 101 is thereby capable of turning inside the pulley case 53 in an angle range defined by each stopper member 68.

Accordingly, the left-right bending pulley 52 is allowed to turn in an angle range combining the angle range allowed for the left-right bending pulley 52 by the auxiliary plate 101 and the angle range allowed for the auxiliary plate 101 by the pulley case 53.

According to such an embodiment, an advantageous effect that the turning angle ranges allowed for the up-down bending pulley 51 and the left-right bending pulley 52 can be appropriately increased may be obtained in addition to the advantageous effects obtained by the embodiment described above.

Figure 33:
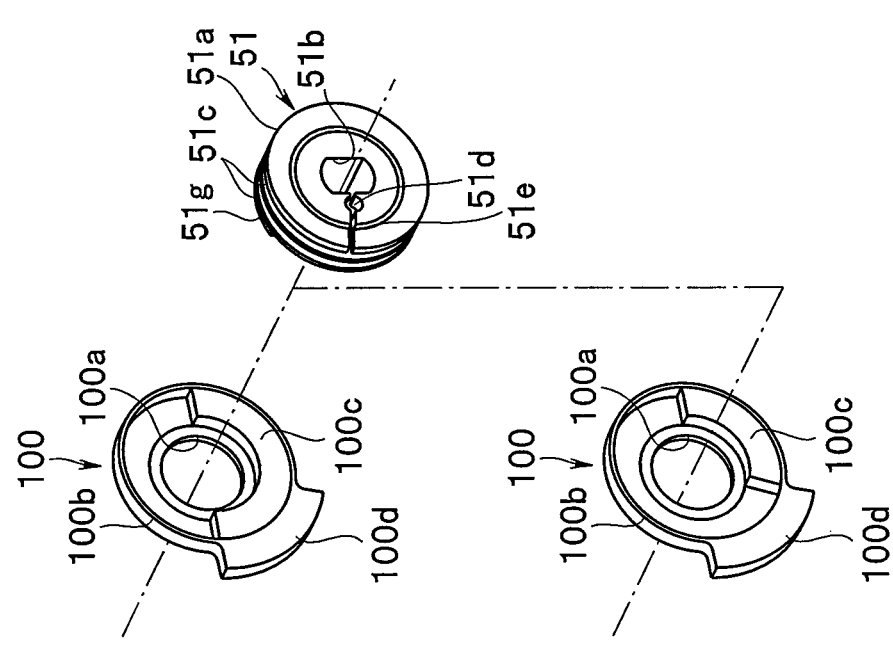
FIG. 33 is a perspective view according to the second embodiment, and shows the auxiliary plate that is selectively used on the up-down bending pulley.

Here, as shown in FIG. 33, the auxiliary plate 100 (and the auxiliary plate 101) can also be replaced as appropriate according to specifications of the endoscope 1 (such as a limit angle of up-down bending or a limit angle of left-right bending), for example.

Figure 34:
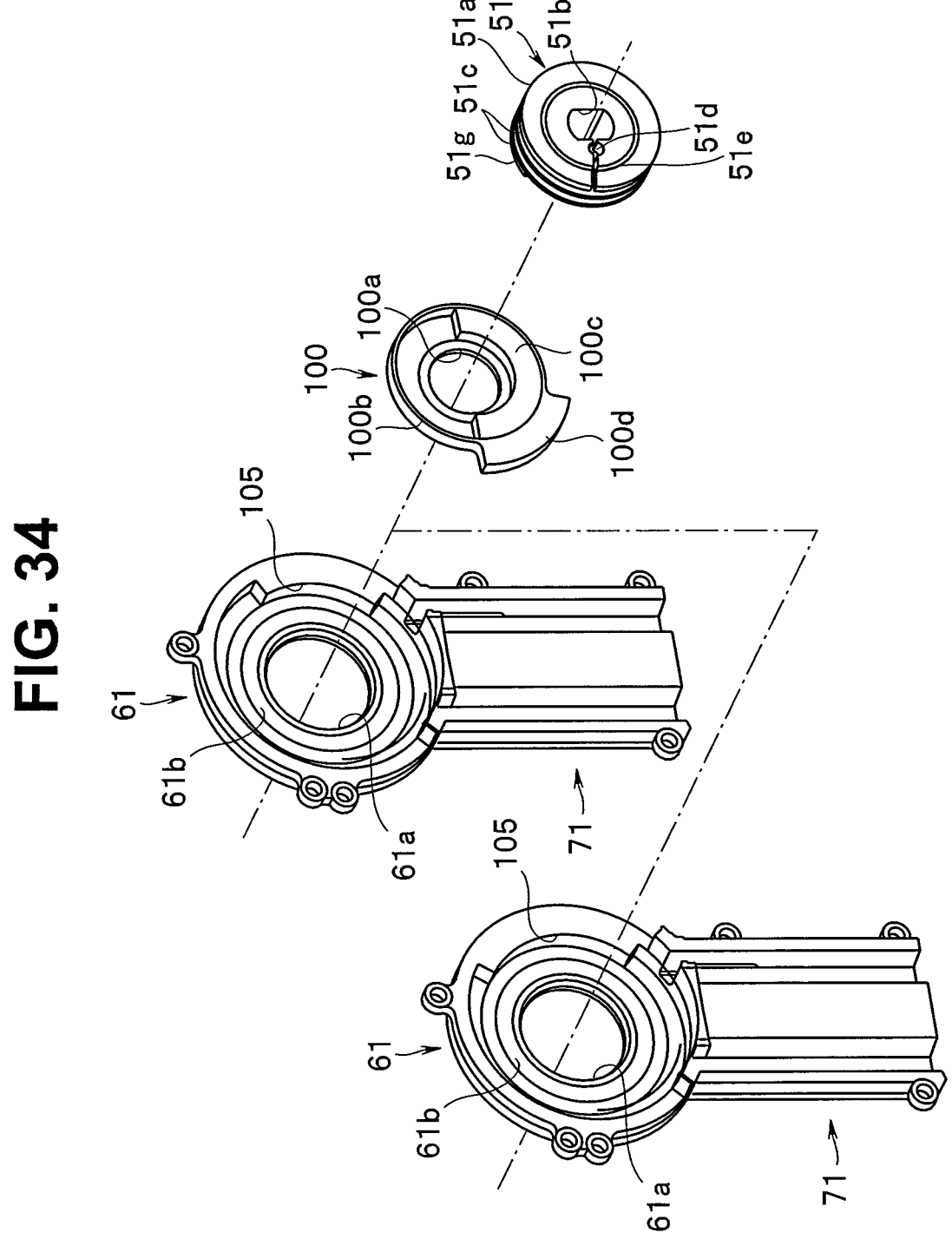
FIG. 34 is a perspective view according to a first modification embodiment, and shows the first case member used selectively for the up-down bending pulley and an auxiliary plate.

As shown in FIG. 34 for example, it is also possible to provide, in the first case member 61 itself, a stopper portion 105 that regulates a rotation angle of the auxiliary plate 100 through contact with the protruding portion 100*d*. In this case, by preparing first case members 61 having a plurality of patterns with different rotation angles regulated by the stopper portion 105 and making the first case members selectively attachable to the housing 15, the endoscope bending operation mechanism 35 that has a simple structure can be manufactured at a low cost by reducing the number of dedicated parts. Although not shown in the drawings, it is of course possible to use the same configuration for the case main body 60, the second case member 62, and the like.

Figure 35:
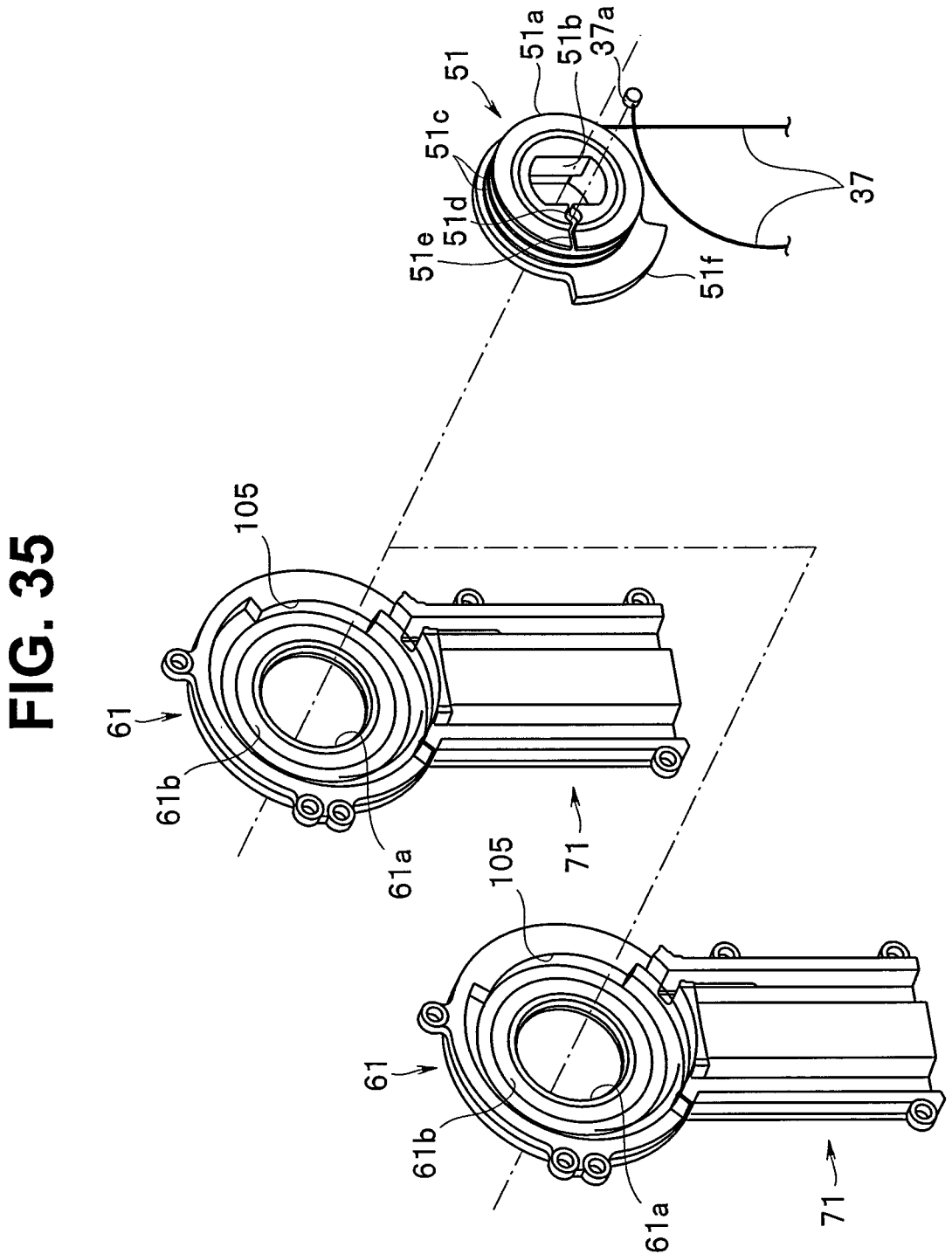
FIG. 35 is a perspective view according to a second modification embodiment, and shows a first case member used selectively for the up-down bending pulley.

Furthermore, as shown in FIG. 35 for example, it is also possible to provide, in the first case member 61 itself, a stopper portion 105 that regulates a rotation angle of the up-down bending pulley 51 through contact with the protruding portion 51*f*. In this case, by preparing first case members 61 having a plurality of patterns with different rotation angles regulated by the stopper portion 105 and making the first case members selectively attachable to the housing 15, the endoscope bending operation mechanism 35 that has a simple structure can be manufactured at a low cost by reducing the number of dedicated parts. Although not shown in the drawings, it is of course possible to use the same configuration for the case main body 60, the second case member 62, and the like.

Note that the present disclosure is not limited to each embodiment described above, and various modifications and changes can be made within the technical scope of the present disclosure.

In other words, the endoscope bending operation mechanism described in each embodiment described above is structured such that the protruding portion is provided on the pulley (the up-down bending pulley and the left-right bending pulley) side and the mounting portion is provided on the pulley case side, but such a configuration is, of course, not restrictive. For example, the endoscope bending operation mechanism can be structured such that the mounting portion is provided on the pulley (the up-down bending pulley and the left-right bending pulley) side and the protruding portion is provided on the pulley case side.

Furthermore, the endoscope bending operation mechanism described in each embodiment described above is structured to bend the bending portion in the up-down direction and the left-right direction, but such a configuration is, of course, not restrictive. For example, the endoscope bending operation mechanism may be structured such that the bending portion is bent in only one of the up-down direction or the left-right direction.

Furthermore, it suffices if at least one mounting portion and at least one stopper member are provided on the endoscope bending operation mechanism. Furthermore, the stopper member may be used in common by the endoscope bending operation mechanisms of different types of endoscopes. For example, a shape of the stopper member mounted on a bending operation mechanism for an endoscope for duodenum and a shape of the stopper member mounted on a bending operation mechanism for an endoscope for large intestine can be made the same. In other words, there may be provided an endoscope system where the stopper member mounted on an endoscope bending operation mechanism for a first endoscope (for example, an endoscope for duodenum) and the stopper member mounted on a bending operation mechanism for a second endoscope (for example, an endoscope for large intestine or an endoscope for stomach) have the same shape.

Furthermore, components of each embodiment described above may, of course, be combined as appropriate.

Example 1. An endoscope bending operation mechanism comprising:
　　a bending operation member;
　　a turning member configured to turn by an operation force from the bending operation member;
　　a long member, a proximal end side of which is wound around the turning member and a distal end side of which is coupled to a bending portion of an insertion section that is inserted into a subject;
　　a holding member that turnably holds the turning member;
　　a stopper member that is attachable to and detachable from one of the holding member or the turning member; and
　　an abutting portion provided on another one of the holding member or the turning member, the abutting portion being configured to restrict a relative rotation angle between the holding member and the turning member by coming into contact with the stopper member, wherein
　　the one of the holding member or the turning member includes a mounting portion where the stopper member is mounted.

Example 2. The endoscope bending operation mechanism according to Example 1, wherein the holding member includes a guide portion that guides the long member that moves in a reciprocating motion.

Example 3. The endoscope bending operation mechanism according to Example 1, wherein the holding member includes, as the mounting portion, a plurality of grooves where the stopper member is selectively mounted, the plurality of grooves being formed radially from a rotation center of the turning member.

Example 4. The endoscope bending operation mechanism according to Example 3, wherein the stopper member includes, in a state of being mounted on the mounting portion, a part that protrudes from the holding member in a direction where the abutting portion is provided.

Example 5. The endoscope bending operation mechanism according to Example 3, comprising two stopper members configured to be mounted on two of the plurality of grooves, wherein the turning member rotates in a range of angles at which the abutting portion abuts against the two stopper members.

Example 6. The endoscope bending operation mechanism according to Example 1, wherein the holding member includes a first holding member, and a second holding member that faces the first holding member, the second holding member sandwiching the turning member with the first holding member, and another turning member configured to turn by an operation force from another bending operation member is further provided on a side of the first holding member that does not face the turning member.

Example 7. The endoscope bending operation mechanism according to Example 6, wherein another long member, an end portion side of which is coupled to the bending portion, is wound around the other turning member.

Example 8. The endoscope bending operation mechanism according to Example 7, comprising a third holding member that faces the other turning member, the third holding member sandwiching the other turning member with the second holding member, wherein a plurality of another mounting portions provided in a circumferential direction of the other turning member are provided on the first holding member or the third holding member, and another stopper member configured to come into contact with the other turning member and restrict a rotation angle of the other turning member is fixed to one of the plurality of other mounting portions.

Example 9. An endoscope comprising:

a bending operation mechanism configured to operate a bending portion provided on an end portion side of an insertion section that is inserted into a subject, wherein the bending operation mechanism includes a bending operation member, a turning member configured to turn by an operation force from the bending operation member, a long member, a proximal end side of which is wound around the turning member and a distal end side of which is coupled to the bending portion, a holding member that turnably holds the turning member, a stopper member that is attachable to and detachable from one of the holding member or the turning member, and an abutting portion provided on another one of the holding member or the turning member, the abutting portion being configured to restrict a relative rotation angle between the holding member and the turning member by coming into contact with the stopper member, and the one of the holding member or the turning member includes a mounting portion where the stopper member is mounted.

Example 10. An endoscope bending operation mechanism comprising:

a bending operation member;

a turning member configured to turn by an operation force from the bending operation member;

a long member wound around the turning member and coupled to the bending portion;

a holding member that is fixed to a housing, and that turnably holds the turning member;

a protruding portion provided on the turning member; and a first stopper portion that is provided on the holding member, the first stopper portion being configured to come into contact with the protruding portion and restrict a rotation angle of the turning member to a first rotation angle.

Example 11. The endoscope bending operation mechanism according to Example 10, wherein the housing allows attachment and detachment of a second holding member, the second holding member including a second stopper portion configured to perform restriction to a second rotation angle different from the first rotation angle.

What is claimed is:

1. An endoscope bending operation mechanism, comprising:

a bending operation controller;

a pulley unit including a pulley supported for rotation by a pulley case, the pulley configured to move by an operation force from the bending operation controller;

a wire having a proximal end and a distal end, wherein the proximal end of the wire is connected to the pulley and the distal end of the wire is connected to a bending portion of an endoscope insertion section; and a movement limiter unit including a limit structure and a stopper structure, wherein the stopper structure and the limit structure are movable relative to each other, wherein an amount of relative rotation between the pulley and the pulley case is restricted by the stopper structure contacting the limit structure, wherein either (i) the limit structure is attachable to and detachable from the pulley case and the pulley includes the stopper structure or (ii) the limit structure is attachable to and detachable from the pulley and the pulley case includes the stopper structure, wherein the pulley case includes a mounting section including three or more grooves, wherein the three or more grooves are arranged in an arc around a center of rotation of the pulley and each of the three or more grooves are oriented radially from the center of rotation of the pulley, wherein the three or more grooves are configured for selectively mounting the limit structure, and wherein the limit structure includes two stoppers configured to be mounted in two of the three or more grooves.

2. The endoscope bending operation mechanism according to claim 1, wherein, when the limit structure is mounted in the mounting section, the limit structure includes a part that protrudes from the pulley case to form an abutting portion of the limit structure that is contacted by the stopper structure and by which the amount of relative rotation between the pulley and the pulley case is restricted.

3. The endoscope bending operation mechanism according to claim 1, wherein the two stoppers are a first stopper configured to be inserted into and protrude from a first groove of the two of the three or more grooves and a second stopper configured to be inserted into and protrude from a second groove of the two of the three or more grooves, and wherein, when the limit structure is mounted in the mounting section with the first stopper inserted into and protruding from the first groove and the second stopper inserted into and protruding from the second groove, an angular separation between the first stopper and the second stopper defines the amount of relative rotation between the pulley and the pulley case.

4. The endoscope bending operation mechanism according to claim 1, wherein the pulley case includes a first pulley housing body and a second pulley housing body that faces the first pulley housing body, wherein, in the pulley case, a first side of the first pulley housing body is oriented toward a first side of the second pulley housing body with the pulley located therebetween, wherein the endoscope bending operation mechanism further comprises:

a second bending operation controller; and a second pulley configured to move by a second operation force from the second bending operation controller, and wherein the second pulley is located on a second side of the first pulley housing body.

5. The endoscope bending operation mechanism according to claim 4, wherein the endoscope bending operation mechanism further comprises a second wire having a proximal end and a distal end, and wherein the proximal end of the second wire is connected to the second pulley and the distal end of the second wire is coupled to the bending portion.

6. The endoscope bending operation mechanism according to claim 5, wherein the pulley case includes a third pulley housing body, wherein, in the pulley case, a first side of the third pulley housing body is oriented toward the second side of the first pulley housing body with the second pulley located therebetween, wherein the endoscope bending operation mechanism further comprises:

a second movement limiter unit including a second limit structure and a second stopper structure, wherein the second stopper structure and the second limit structure are movable relative to each other, wherein an amount of relative rotation between the second pulley and the pulley case is restricted by the second stopper structure contacting the second limit structure, and wherein either (i) the second limit structure is attachable to and detachable from the first pulley housing body or the third pulley housing body and the second pulley includes the second stopper structure or (ii) the second limit structure is attachable to and detachable from the second pulley and the first pulley housing body or the third pulley housing body includes the second stopper structure.

7. The endoscope bending operation mechanism according to claim 6, wherein the third pulley housing body mates to the second pulley housing body.

8. An endoscope, comprising an operation section disposed proximally relative to the endoscope insertion section, the operation section including the endoscope bending operation mechanism according to claim 1, the endoscope bending operation mechanism configured to operate the bending portion.

9. The endoscope according to claim 8, wherein the endoscope insertion section extends in a longitudinal direction, and wherein the pulley case includes a guide portion configured to guide the wire to move in the longitudinal direction.

10. An endoscope bending operation mechanism, comprising:

a bending operation controller;

a pulley configured to move by an operation force from the bending operation controller;

a pulley case supporting the pulley for rotation;

a wire having a proximal end and a distal end, wherein the proximal end of the wire is connected to the pulley and the distal end of the wire is connected to a bending portion of an insertion section of an endoscope that is configured to insert into a subject; and two limit structures, wherein the pulley case includes three or more slit-shaped recessed grooves, two of the three or more slit-shaped recessed grooves are configured to mount the two limit structures, and wherein the three or more slit-shaped recessed grooves are arranged in an arc around a center of rotation of the pulley and each of the three or more slit-shaped recessed grooves are oriented radially from the center of rotation of the pulley.

11. The endoscope bending operation mechanism according to claim 10, wherein the pulley includes a stopper structure, an amount of relative rotation between the pulley and the pulley case is restricted by the stopper structure contacting two limit structures.

12. The endoscope bending operation mechanism according to claim 11, wherein, when the two limit structures are mounted in the two of the three or more slit-shaped recessed grooves, the two limit structures include a part that protrudes from the pulley case to abut on the stopper structure.

13. The endoscope according to claim 8, wherein, when the limit structure is mounted in the mounting section, the limit structure includes a part that protrudes from the pulley case to form an abutting portion of the limit structure that is contacted by the stopper structure and by which the amount of relative rotation between the pulley and the pulley case is restricted.

14. The endoscope according to claim 10, wherein the two limit structures are a flat plate.

* * * * *